US006762164B2

(12) United States Patent
Kim et al.

(10) Patent No.: US 6,762,164 B2
(45) **Date of Patent: *Jul. 13, 2004**

(54) USE OF 3-POSITION CYCLOSPORIN DERIVATIVES FOR HAIR GROWTH

(75) Inventors: Sang-Nyun Kim, Daejeon (KR); Ho-Jeong Ahn, Daejeon (KR); Chang-Woo Lee, Daejeon (KR); Min-Ho Lee, Daejeon (KR); Jung-Hun Kim, Daejeon (KR); Jong-Il Kim, Daejeon (KR); Seung-Jin Kim, Seoul (KR); Ho-Song Cho, Daejeon (KR); Heon-Sik Lee, Daejeon (KR); Hyung-Jin Kim, Daejeon (KR)

(73) Assignee: LG Household & Health Care Ltd., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 10/303,281

(22) Filed: Nov. 25, 2002

(65) Prior Publication Data

US 2003/0207798 A1 Nov. 6, 2003

Related U.S. Application Data

(62) Division of application No. 10/141,723, filed on May 9, 2002.

(30) Foreign Application Priority Data

May 11, 2001 (KR) ........................................ 2001-25682

(51) Int. Cl.[7] ........................... A61K 38/13; C07K 7/64

(52) U.S. Cl. .......................................... 514/11; 530/321

(58) Field of Search ....................... 514/9, 11; 530/317, 530/321

(56) References Cited

U.S. PATENT DOCUMENTS

| | | | | | |
|---|---|---|---|---|---|
| 4,771,122 | A | * | 9/1988 | Seebach | 530/317 |
| 5,807,820 | A | | 9/1998 | Elias | 514/11 |
| 5,948,884 | A | * | 9/1999 | Luchinger | 530/317 |
| 5,994,299 | A | * | 11/1999 | Barriere et al. | 514/11 |
| 6,521,595 | B1 | * | 2/2003 | Kim et al. | 514/11 |
| 6,583,265 | B1 | * | 6/2003 | Ellmerer-Muller et al. | 530/317 |
| 2001/0025025 | A1 | * | 9/2001 | Kiskov | 514/9 |
| 2002/0165133 | A1 | * | 11/2002 | Kim et al. | 514/9 |

FOREIGN PATENT DOCUMENTS

| | | | | |
|---|---|---|---|---|
| EP | 0 414 632 | B1 | | 10/1996 |
| GB | 2 218 334 | A | | 11/1989 |
| JP | 60-243008 | A | | 12/1985 |
| JP | 62-019512 | A | | 1/1987 |
| JP | 62-019513 | A | | 1/1987 |
| WO | WO 93/17039 | A1 | | 9/1993 |
| WO | WO-00/51558 | A1 | * | 9/2000 |

OTHER PUBLICATIONS

Seebach et al Modification of Cyclosporin A . . . Helvetica Chimca Acta. 1993, vol. 76, pp. 1564–1590.*

Maurer et al., "Hair Growth Modulation by Topical Immunophilin Ligands," *American Journal of Pathology*, 1997, pp. 1433–1441, vol. 150, No. 4.

Eberle et al., "Cyclosporin A: Regioselective Ring Opening and Fragmentation Reactions via Thioamides. A Route to Semisynthetic Cyclosporins," *J. Org. Chem.*, 1994, pp. 7249–7258, vol. 59, No. 24.

Lutz, "Effects of Cyclosporin A on Hair," *Skin Pharmacol.*, 1994, pp. 101–104, vol. 7.

Eberle et al., "Preparation of [D–Cysteine]–cyclosporin via Intramolecular Sulfur Transfer Reaction," *J. Org. Chem.*, 1993, pp. 673–677, vol. 58, No. 3.

Seebach et al., "Thiocyclosporins: Preparation, Solution and Crystal Structure, and Immunosuppressive Activity," *Helv. Chim. Acta*, 1991, pp. 1953–1990, vol. 74.

Gilhar et al., "Topical cyclosporine in male pattern alopecia," *J. Am. Acad. Dermatol.*, 1990, pp. 251–253, vol. 22, No. 2.

Gupta et al., "Oral cyclosporine for the treatment of alopecia areata," *J. Am. Acad. Dermatol.*, 1990, pp. 242–250, vol. 22, No. 2.

Von Traber et al., "Novel Cyclosporins from *Tolypociadium inflatum*. The Cyclosporins K–Z," *Helv. Chim. Acta*. 1987, pp. 13–36, vol. 70.

* cited by examiner

*Primary Examiner*—Jeffrey E. Russel

(74) *Attorney, Agent, or Firm*—Webb Ziesenheim Logsdon Orkin & Hanson, P.C.

(57) ABSTRACT

Disclosed is a hair growth promoting agent including a cyclosporin derivative as an active ingredient, and more particularly, a hair growth promoting agent including a cyclosporin A derivative substituted in the 3-position as an active ingredient.

4 Claims, 14 Drawing Sheets

1H of I 13C of J 1H of CW-273

13C of CW-273

1H of P

USE OF 3-POSITION CYCLOSPORIN DERIVATIVES FOR HAIR GROWTH

CROSS REFERENCE TO RELATED APPLICATION

This application is a divisional of U.S. patent application Ser. No. 10/141,723, filed May 9, 2002.

TECHNICAL FIELD

The present invention relates to a hair growth promoting agent comprising a cyclosporin derivative as an active ingredient and more particularly, to a hair growth promoting agent comprising cyclosporin derivatives modified in the 3-position as an active ingredient.

BACKGROUND ART

On average, the human scalp contains about 100,000 to 150,000 hairs. Each hair has three main stages of growth: anagen, catagen and telogen, after which the hair falls out. This hair growth cycle is repetitive and the duration of one cycle is different from other cycles, ranging approximately 3 to 6 years. Thus, the average adult normally loses about 50 to 100 hairs every day. In general, alopecia refers to a phenomenon wherein duration of the anagen growth phase is shortened and the percentage of hairs in the catagen and telogen phases increases, whereby the number of lost hairs is increased excessively and abnormally.

There are many theories to explain for loss of hair, including for example, poor blood circulation, excessive functioning of male sex hormone, excessive production and secretion of sebum, deterioration of scalp by peroxides, bacteria, etc., hereditary factors, aging, stress, etc. However, explicit mechanisms have not been revealed. Recently, the population suffering from hair loss is tending to increase, since changing dietary habits and stress imposed on individuals due to modem social environments, etc. has increased. Also, the age of the individuals affected by alopecia is dropping and furthermore, the population of female alopecia sufferers is rising.

One of preparations which are most commonly used for treatment and prevention of alopecia is one that contains minoxidil. There are two hair-regrowth agents which have received approval from the U.S. Food and Drug Administration, and minoxidil is one of those approved hair-regrowth agents. Minoxidil was originally developed as a hypertension drug for the purpose of reducing blood pressure. However, when using this drug, as a side effect, a trichogenous effect was observed and thereafter, this drug became famous as a hair-regrowth agent. Although mechanisms by which minoxidil works as a hair-regrowth agent is not clearly understood, it is inferred that minoxidil increases blood flow by expansion of blood vessels, whereby roots of hairs are supplied with more nutrition and eventually, growth of hairs are promoted.

Such a model of blood flow increase has been indirectly supported by a recent report that minoxidil enhances the expression of vascular endothelial growth factor (VEGF), a growth factor associated with vasodilatation in the dermal papilla which is a main cell making up the hair roots. Also, other than the vasodilative effect of the minoxidil in the hair-restoring mechanism, it has been reported that minoxidil promotes activation of dermal papilla cells in the roots of hair incubated in vitro, and growth of hair follicles in a tissue culture of follicles in vitro. These facts indicate that minoxidil may work directly on the roots of hair as a growth factor.

In addition, finasteride, a main component of Propecia which has started to be sold by Merck, is used for treatment of alopecia. It inhibits conversion of the male hormone testosterone into dihydrotestosterone, which is a more potent male hormone than testosterone. On December of 1997, the 1 mg finasteride tablet was approved by the US FDA as a hair-regrowth agent for treatment of male pattern hair loss in men only, and is now commercially available. In clinical studies, it has been demonstrated to have a significant trichogenous effect. However, there has been a report that finasteride may inhibit male sexual function as a side effect. Since neither finasteride nor minoxidil show superior effect in clinical tests, and there is concern about side effects, many researches are conducted to develop a new and improved hair-regrowth agents.

The cyclosporin family of drugs has immunosuppressive activity. It is also effective to inhibit growth of virus, fungus, protozoan, etc. and has various physiological effects such as nephrotoxicity, hepatotoxicity, hypertension, enlargement of periodontium, trichogenous effect, and so on, as side effects. Cyclosporin A, a representative cyclosporin, is a cyclic peptide having the following Chemical Formula, which comprises 11 amino acids, including several N-methyl amino acids and D-alanine at No. 8 residue.

[Structure Formula 1]

| MeBmt- | Abu- | Sar- | MeLeu- | Val- | MeLeu- | Ala- | DAla- | MeLeu- | MeLeu- | MeVal |
|---|---|---|---|---|---|---|---|---|---|---|
| 1 | 2 | 3 | 4 | 5 | 6 | 7 | 8 | 9 | 10 | 11 |

where MeBmt is N-methyl-(4R)-4-[(E)-2-butenyl]-4-methyl-L-threonine, Abu is L-α-aminobutyric acid, Sar is sarco-sine, MeLeu is N-methyl-L-leucine, Val is L-valine, Ala is L-alanine, DAla is D-alanine, MeVal is N-methyl-L-valine.

The amino acid form of cyclosporin A of the above Chemical Formula 1 is L-configuration, unless otherwise specified. The residue numbering of amino acids starts from MeBmt and proceeds clockwise, i.e. 1 for MeBmt and 11 for the last MeVal (N-methyl-L-valine) as shown in the Structure Formula 1. Nomenclature of various derivatives including cyclosporins A to Z, follows methods commonly used (Helv. Chim. Acta, 1987, 70:13–36). For example, if Abu in the 2-position of cyclosporin A is substituted with L-alanine, L-threonine, L-valine or L-norvaline, the derivatives thus prepared are named cyclosporin B, cyclosporin C, cyclosporin D or cyclosporin G, respectively. Further, when the amino acid residues of the cyclosporin derivatives differ from those of cyclosporin A, the derivatives are named by describing the substituent. For example, if sarcosine, being the amino acid residue 3 of cyclosporin A, is substituted with N-methyl-D-$Abu^3$ or N-methyl-D-$Nva^3$, the derivatives thus prepared are named [N-methyl-D-$Abu^3$] cyclosporin A or [N-methyl-D-$Nva^3$] cyclosporin A, respectively. Meanwhile, a common method for abbreviating amino acids is employed, that is, N-methyl-L-leucine is abbreviated by MeLeu, N-methyl-L-isoleucine by MeIle, N-methyl-L-Valine by MeVal, N-methyl-L-alanine by MeAla, N-methyl-L-norvaline by MeNva, L-leucine by Leu, L-isoleucine by Ile, sarcosine by Sar, L-serine by Ser, L-valine, Val, L-alanine by Ala, D-alanine by DAla, L-aminobutyric acid by Abu, L-threonine by Thr, and L-norvaline by Nva. Further, as for a derivative of cyclosporin which is substituted with sulfur instead of a carbonyl oxygen at the amino acid residue 7, the name of the derivative may be cyclosporin 7-thioamide or [$^7\psi^8$ CS—NH] cyclosporin, according to different references (Helv. Chim. Acta. 74:

1953–1990, 1991; J. Org. Chem. 58: 673–677, 1993; J. Org. Chem. 59: 7249–7258, 1994).

So far, possible development of cyclosporin as a hair-regrowth agent has been studied by many research groups. Particularly, researches involving animal hair regrowth tests, human alopecia areata (J. Am. Acad. Dermatol., 1990, 22:242–250), human male pattern alopecia (J. Am. Acad. Dermatol., 1990, 22:251–253 and Skin Pharmacol., 1994, 7:101–104), and inhibition effect of hair loss by chemotherapy in animal models (Am. J. Pathol., 1997, 150:1433–1441) have been widely conducted. In comparative experiments on mouse's back, it is shown that cyclosporin has a hair regrowth effect about 100 times superior to minoxidil Based on such findings, there have been attempts to utilize cyclosporin as a treatment for male pattern alopecia, and many applications for patents have been filed.

For example, Japanese Patent Publication Kokai Nos. Sho 60-243008, Sho 62-19512 and Sho 62-19513 disclose use of cyclosporin derivatives as a hair regrowth agent. Also, Europe Patent Publication No. 0414632B1 teaches a cyclosporin derivative modified in the 8-position, and PCT Publication No. 93/17039 teaches isocyclosporin. Moreover, U.S. Pat. No. 5,807,820 and British Patent No. 2,218,334A disclose cyclosporins with excellent transdermal absorption, pursuant to the use of cyclosporins as hair restorers.

DISCLOSURE OF THE INVENTION

Therefore, the present invention has been made in view of the above problems associated with side effects of cyclosporin A, and it is an object of the present invention to provide a hair growth promoting agent comprising a cyclosporin derivative as an active ingredient, which exerts an excellent hair growth-promotion ability.

In accordance with one aspect of the present invention, the above and other objects can be accomplished by the provision of a hair growth promoting agent comprising a 3-position analog of cyclosporin represented by the below Formula 1, as an active ingredient, which is prepared by synthesizing a variety of derivatives thereof and evaluating their hair growth promoting effects, with an aim of developing a novel agent for promoting hair growth.

[Formula 1]

A—B—C—D—E—F—G—H—I—J—K (cyclic: A linked to K)

wherein:

A represents N-methyl-(4R)-4-[(E)-2-butenyl]-4-methyl-L-threonine, (2S,3R,4R,6E)-3-sulfhydryl-4-methyl-2-(methylamino)-6-octenoic acid or (2S,4R,6E)-3-oxo-4-methyl-2-(methylamino)-6-octenoic acid;

B represents L-aminobutyric acid (Abu), L-alanine (Ala), L-threonine (Thr), L-valine (Val) or L-norvaline (Nva);

C represents a D-amino acid represented by the general formula 1, $CH_3NH—CH(R)—COOH$ [General formula 1]

in which,

R is one selected from the group consisting of hydrogen, $C_1$–$C_6$ straight or branched alkyl, alkenyl or alkynyl moieties, substituted or unsubstituted with one or more selected from the group consisting of amino, hydroxy, halo, haloalkyl, ester, alkoxy, cyano, nitro, alkylamino, and dialkylamino, and X—R' represented by the general formula 2 below, —X—R' [General formula 2]

in which,

X is oxygen or sulfur, and

R' is one selected from the group consisting of hydrogen, and $C_1$–$C_6$ straight or branched alkyl, alkenyl or alkynyl moieties, substituted or unsubstituted with one or more selected from the group consisting of amino, hydroxy, halo, haloalkyl, ester, alkoxy, cyano, nitro, alkylamino, and dialkylamino;

D represents N-methyl-L-leucine, γ-hydroxy N-methyl-L-leucine or L-valine;

E represents L-valine or L-norvaline;

F represents N-methyl-L-leucine, y-hydroxy N-methyl-L-leucine or L-leucine;

G represents L-alanine or L-alanine thioamide ([$^7\psi^8$CS—NH], NH—$CHCH_3$—CS—);

H represents a D-amino acid represented by the general formula 3,

—NH—$CH(CH_2R)$—COOH [General formula 3]

in which,

R is hydrogen or X—R' represented by the general formula 4,

—X—R' [General formula 4]

in which,

X is oxygen or sulfur, and

R' is one selected from the group consisting of hydrogen, and $C_1$–$C_6$ straight or branched alkyl, alkenyl or alkynyl moieties, substituted or unsubstituted with one or more selected from the group consisting of amino, hydroxy, halo, haloalkyl, ester, alkoxy, cyano, nitro, alkylamino, and dialkylamino;

I represents N-methyl-L-leucine, -γ-hydroxy-N-methyl-L-leucine or L-leucine;

J represents N-methyl-L-leucine, -γ-hydroxy-N-methyl-L-leucine or L-leucine; and, K represents N-methyl-L-valine or L-valine.

In accordance with another aspect of the invention, there is provided a hair growth promoting agent comprising a 3-position analog of cyclosporin with an excellent hair growth promoting effect, represented by Formula 2 below, as an active ingredient.

[Formula 2]

MeBmt—A'—B'—C'—D'—E'—F'—G'—H'—I'—J'—K'—MeVal (cyclic: MeBmt linked to MeVal)

wherein:

MeBmt represents N-methyl-(4R)-4-[(E)-2-butenyl]-4-methyl-L-threonine;

A' represents L-aminobutyric acid, L-alanine, L-threonine, L-valine or L-norvaline;

B' represents N-methyl-D-aminobutyric acid, N-methyl-D-norvaline, D-2-(methylamino)hexa-4-ynoyl, D-2-(methylamino)pent-4-ynoyl, D-2-methylthio-sarcosine, N-methyl-O-propenyl-D-serine or N-methyl-D-serine;

C'represents N-methyl-L-leucine, γ-hydroxy-N-methyl-L-leucine or L-valine;

D'represents L-valine or L-norvaline;

E'represents N-methyl-L-leucine, γ-hydroxy N-methyl-L-leucine or L-leucine;

F'represents L-alanine or L-alanine thioamide ([$^7\psi^8$CS—NH], NH—$CHCH_3$—CS—);

G'represents D-alanine or D-serine;

H'represents N-methyl-L-leucine, γ-hydroxy N-methyl-L-leucine or L-leucine;

I'represents N-methyl-L-leucine, γ-hydroxy N-methyl-L-leucine or L-leucine; and, MeVal represents N-methyl-L-valine.

In accordance with another aspect of the invention, there is provided a hair growth promoting agent comprising a 3-position analog of cyclosporin with an excellent hair growth promoting effect, represented by Formula 3 below, as an active ingredient,

[Formula 3]

[Formula 3]

MeBmt—A″—B″—MeLeu-Val-MeLeu-Ala-DAla-MeLeu-MeLeu-MeVal wherein:

MeBmt represents N-methyl-(4R)-4-[(E)-2-butenyl]-4-methyl-L-threonine;

A" represents L-alanine, L-threonine, L-valine or L-norvaline;

B" represents N-methyl-D-aminobutyric acid, N-methyl-D-norvaline, D-2-(methylamino)hexa-4-ynoyl, D-2-(methylamino)pent-4-ynoyl, D-2-methylthio-sarcosine, N-methyl-O-propenyl-D-serine or N-methyl-D-serine;

MeLeu represents N-methyl-L-leucine;

Val represents L-valine;

Ala represents L-alanine;

DAla represents D-alanine; and,

MeVal represents N-methyl-L-valine.

In accordance with yet another aspect of the present invention, there is provided a hair growth promoting agent, whose composition comprising a 3-position analog of cyclosporin may be formulated in the form of liquid formulations, sprays, gels, pastes, emulsions, creams, conditioners or shampoos.

BRIEF DESCRIPTION OF THE DRAWINGS

The above and other objects, features and other advantages of the present invention will be more clearly understood from the following detailed description taken in conjunction with the accompanying drawing, in which.

BEST MODE FOR CARRYING OUT THE INVENTION

Hereinafter, the present invention will be described in detail, in conjunction with various examples. These examples are provided only for illustrative purposes, and the present invention is not to be construed as being limited to those examples.

With the aim of developing a novel agent with hair growth promoting effect, the present inventors chemically synthesized a variety of 3-position analogs of cyclosporin, and hair growth promoting effects thereof were examined. Thus, the invention provides a hair growth promoting agent comprising a cyclosporin derivative as an active ingredient,

EXAMPLE 1

Synthesis of 3-position Analog of Cyclosporin

A general method for the alkylation of cyclosporin A was as follows. Tetrahydrofuran (THF) was added with diisopropyl amine ((i-Pr)$_2$NH) and added with a solution of n-butyl lithium (BuLi) in hexane under nitrogen atmosphere at −78° C., followed by stirring for 30 min. To the solution of LDA (lithium dilsopropylamide) thus prepared, cyclosporin A in THF was added, stirred for 1 hr, and electrophile was added.

1–1: Synthesis of [N-methyl-D-Abu3] cyclosporin A: Compound 1

According to the general method above, to a solution of 10 equivalents of LDA was added 1.0 g cyclosporin A in 50 ml THF at −78° C. The reaction mixture was stirred for 2 hrs at −78° C. and added with 0.4 ml ethyliodide. After the temperature of the solution reached room temperature, the solution was further stirred for 24 hrs and added with 20 ml water, followed by concentration. The residue was added with ether ($Et_2O$), washed with water and a solution of saturated sodium chloride in sequence, and dried over anhydrous $MgSO_4$. After concentrating, the residue was subjected to silica gel column chromatography (100 g silica gel, dichloromethane:methylalcohol=96:4), followed by HPLC to give 0.1 g of the title compound.

Figure 1:
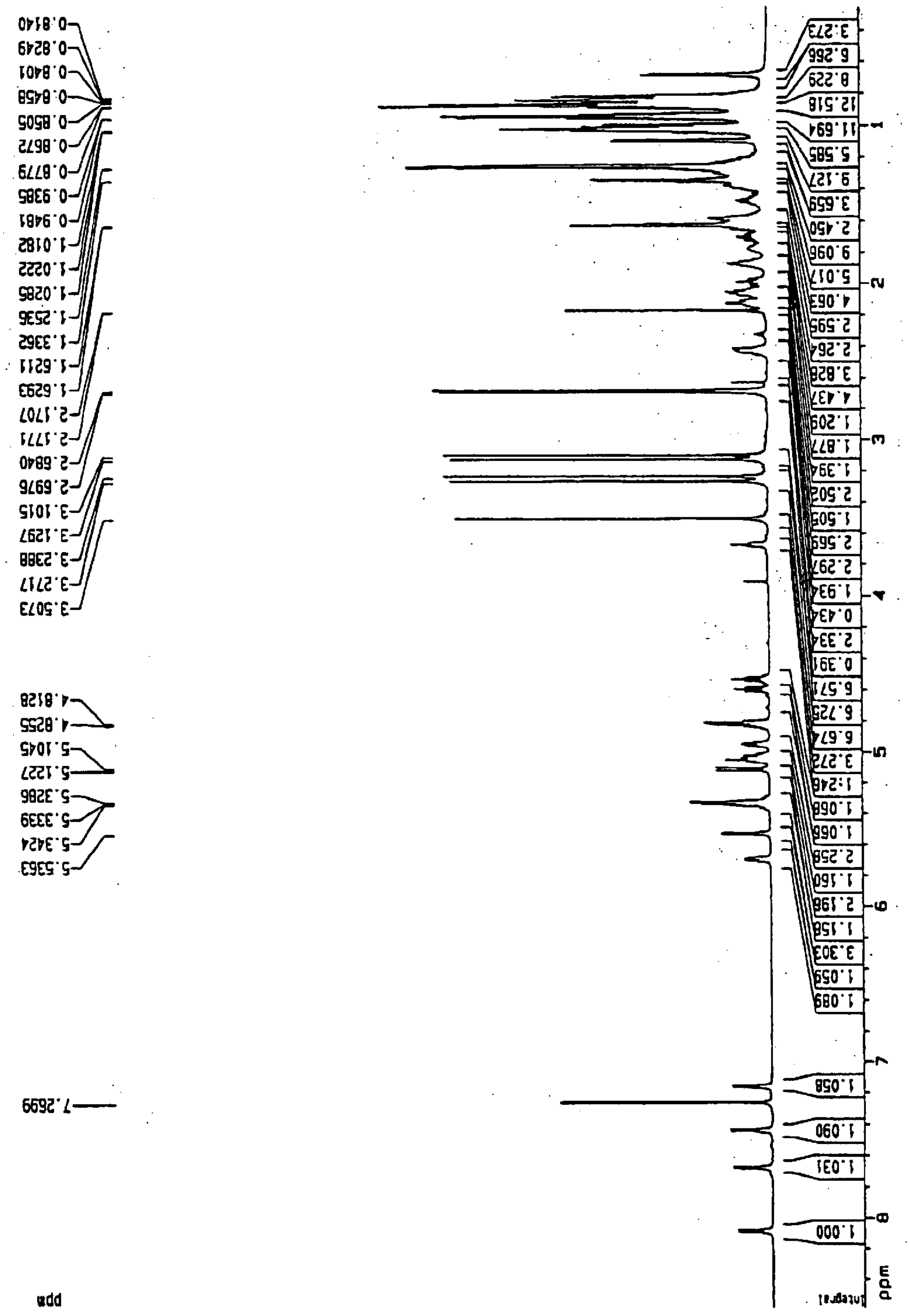
FIG. 1 is a $^1$H-NMR spectrum of [N-methyl-D-Abu$^3$] cyclosporin A.
Figure 2:
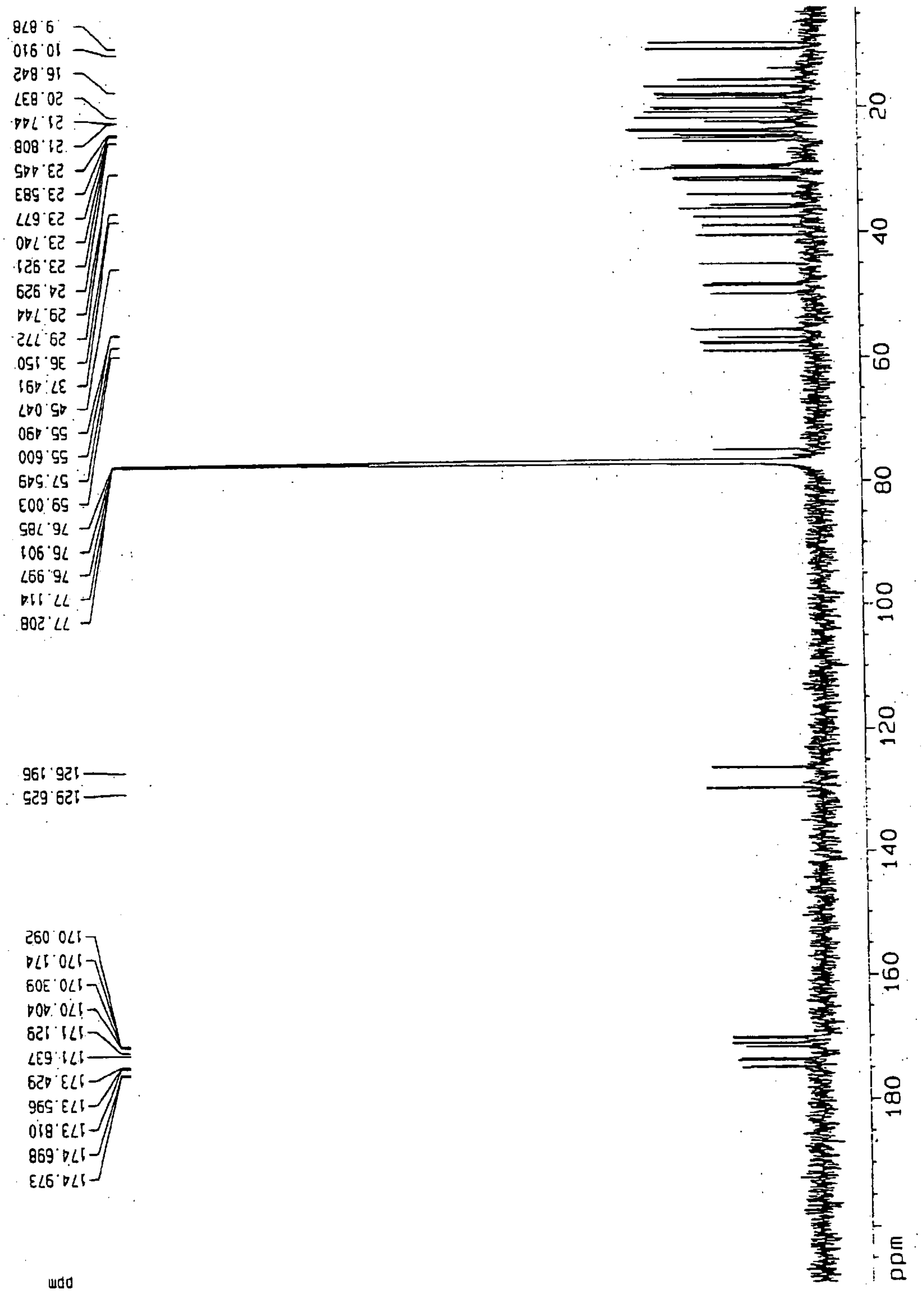
FIG. 2 is a $^{13}$C-NMR spectrum of [N-methyl-D-Abu$^3$] cyclosporin A.

Molecular weight of the compound was determined by FAB MS (ZMS AX 505H) analysis. To confirm the molecular structure, Nuclear Magnetic Resonance (NMR) measurements were performed on 600 MHz (Bruker) for $^1$H-NMR and on 150 MHz (Bruker) for $^{13}$C-NMR, and the spectra are shown in FIGS. 1 and 2, respectively.

1–2: Synthesis of [N-methyl-D-Nva$^3$] cyclosporin A: Compound 2

Figure 3:
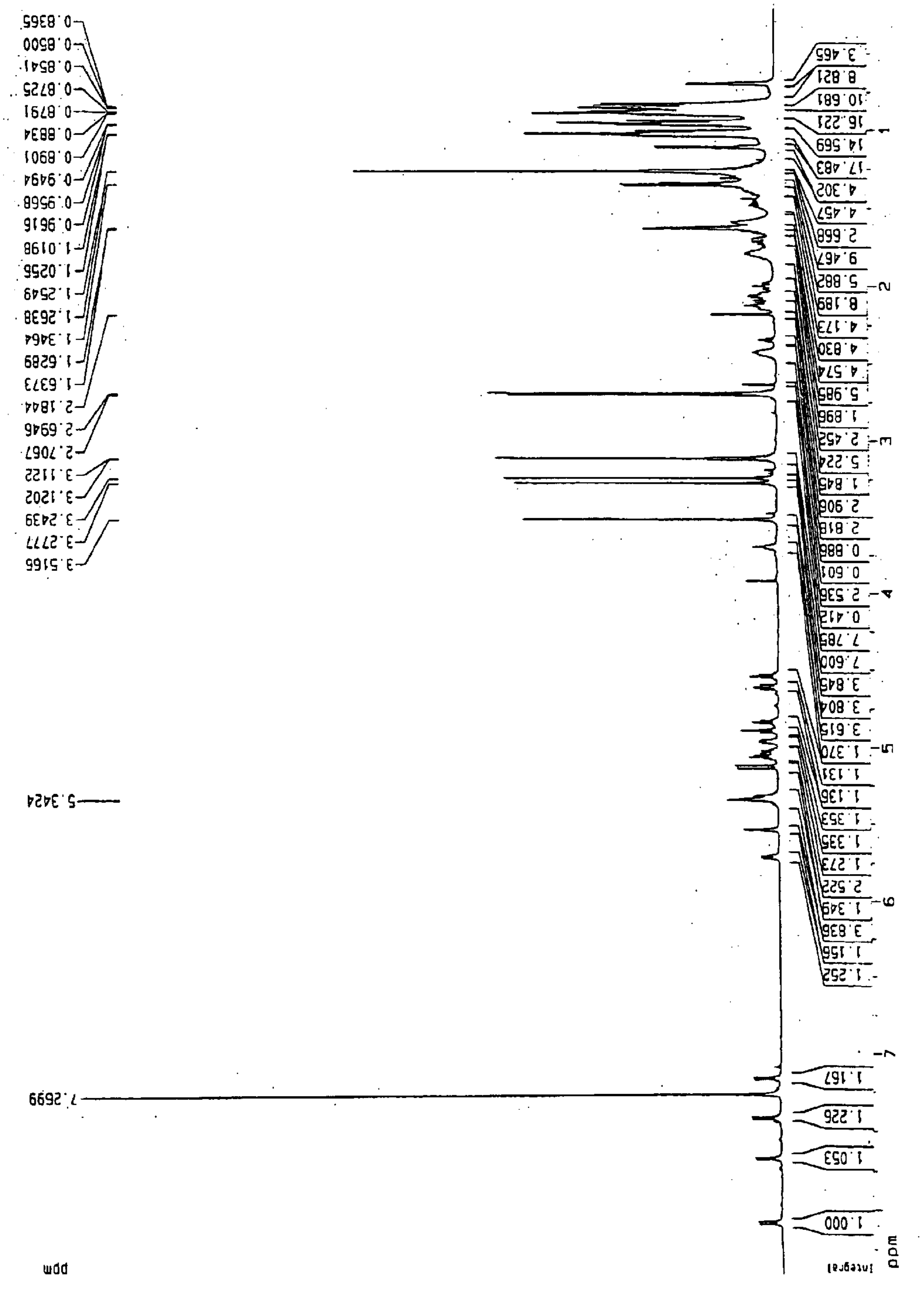
FIG. 3 is a $^1$H-NMR spectrum of [N-methyl-D-Nva$^3$] cyclosporin A.
Figure 4:
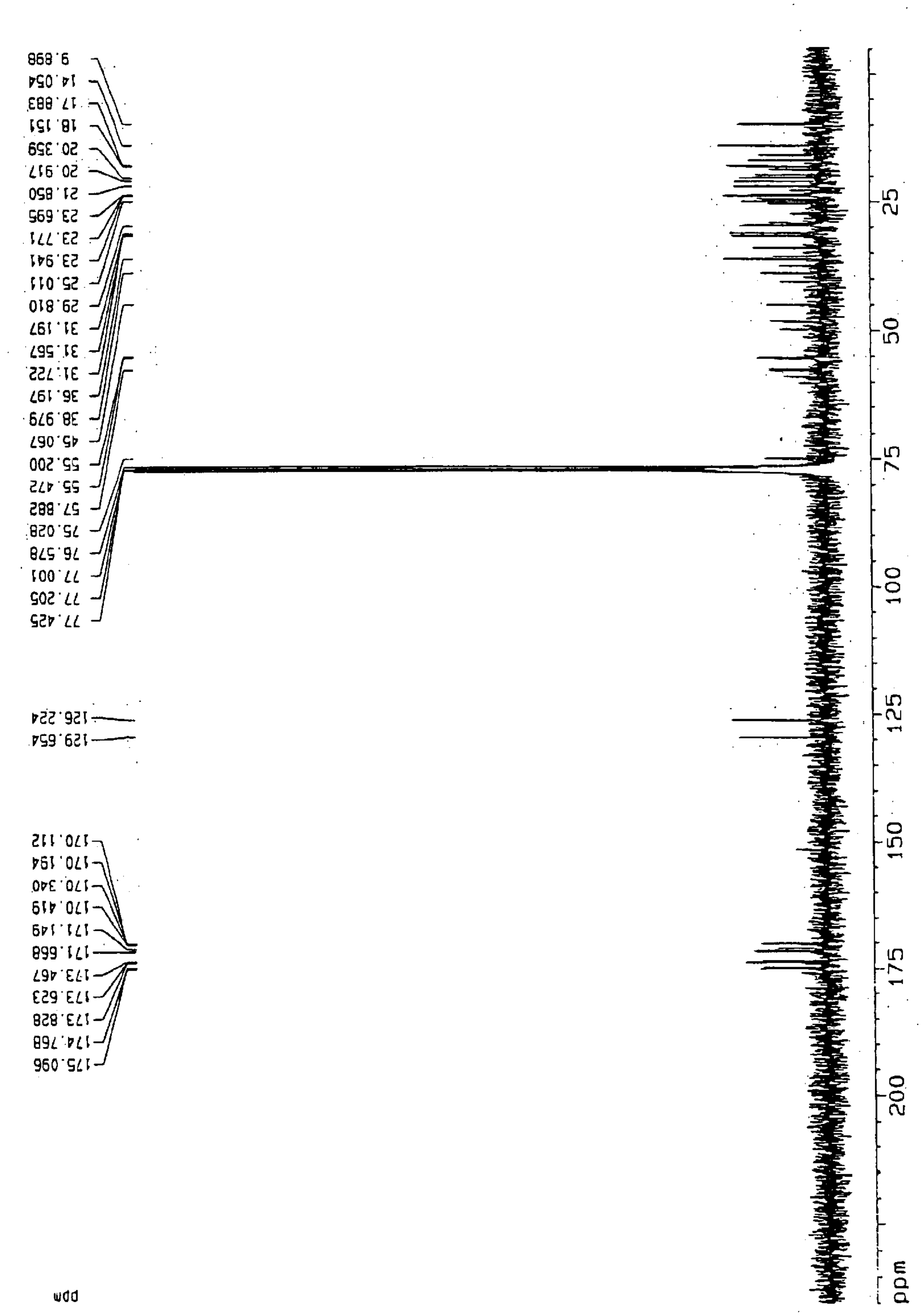
FIG. 4 is a $^{13}$C-NMR spectrum of [N-methyl-D-Nva$^3$] cyclosporin A.

According to the general method, to a solution of 10 equivalents of LDA was added 1.0 g cyclosporin A in 50 ml THF at −78° C. The reaction mixture was stirred for 2 hrs at −78° C. and added with 0.41 ml propyliodide. After the temperature of the solution reached room temperature, the solution was further stirred for 24 hrs and added with 20 ml water, followed by concentration. The residue was added with ether ($Et_2O$), washed with water and a solution of saturated sodium chloride in sequence, and dried over anhydrous $MgSO_4$. After concentrating, the residue was subjected to silica gel column chromatography (100 g silica gel, dichloromethane:methylalcohol=96:4), followed by HPLC to give 0.12 g of the title compound. Molecular weight of the compound was determined by FAB MS (ZMS AX 505H) analysis. To confirm the molecular structure, Nuclear Magnetic Resonance (NMR) measurements were performed on 600 MHz (Bruker) for $^1$H-NMR and on 150 MHz (Bruker) for $^{13}$C-NMR, and the spectra are shown in FIGS. 3 and 4, respectively.

1–3: Synthesis [D-2-(methylamino)hexa-4-ynoyl$^3$] cyclosporin A: Compound 3

Figure 5:
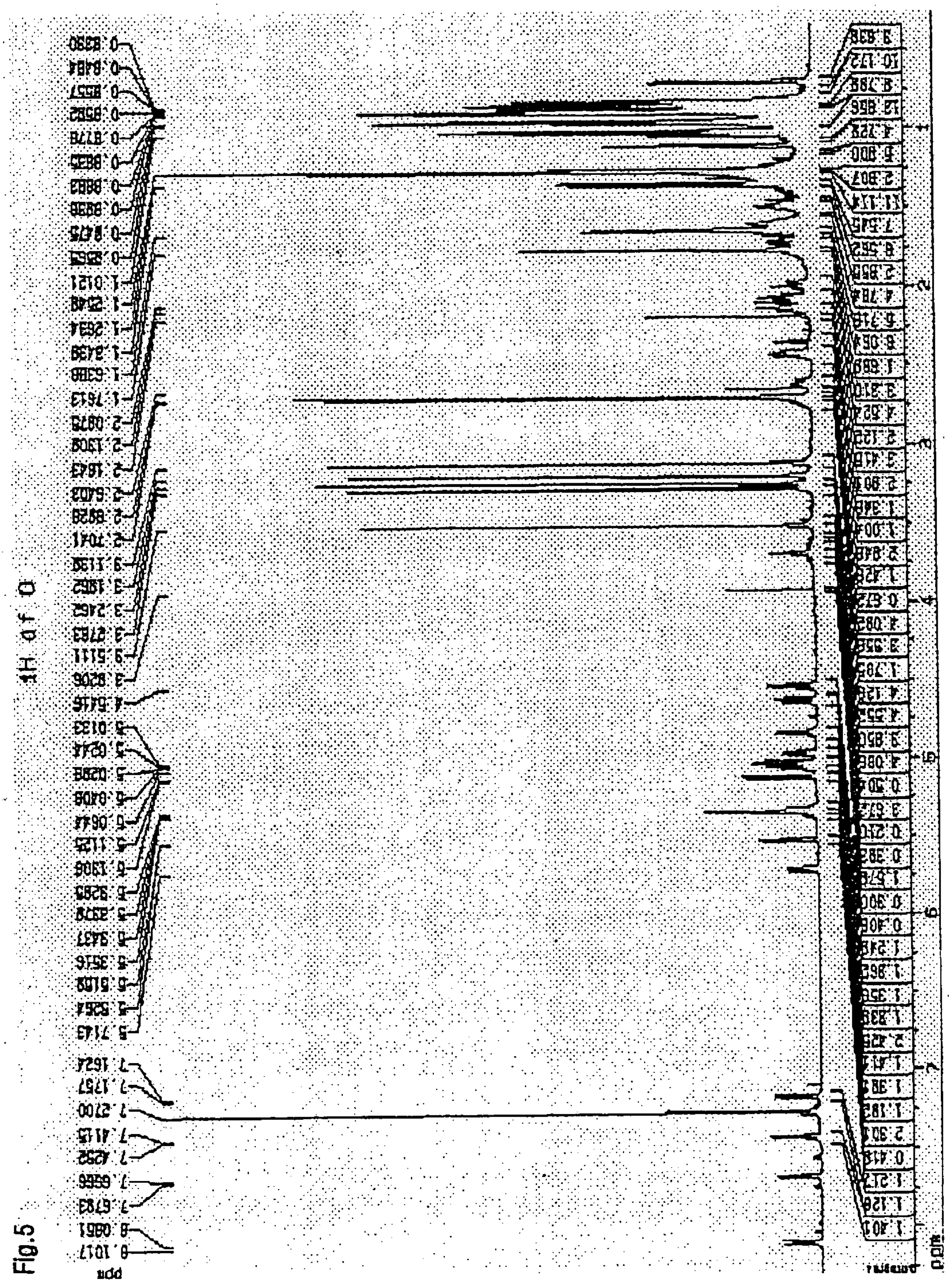
FIG. 5 is a $^1$H-NMR spectrum of [D-2-(methylamino) hexa-4-ynoyl$^3$] cyclosporin A.
Figure 6:
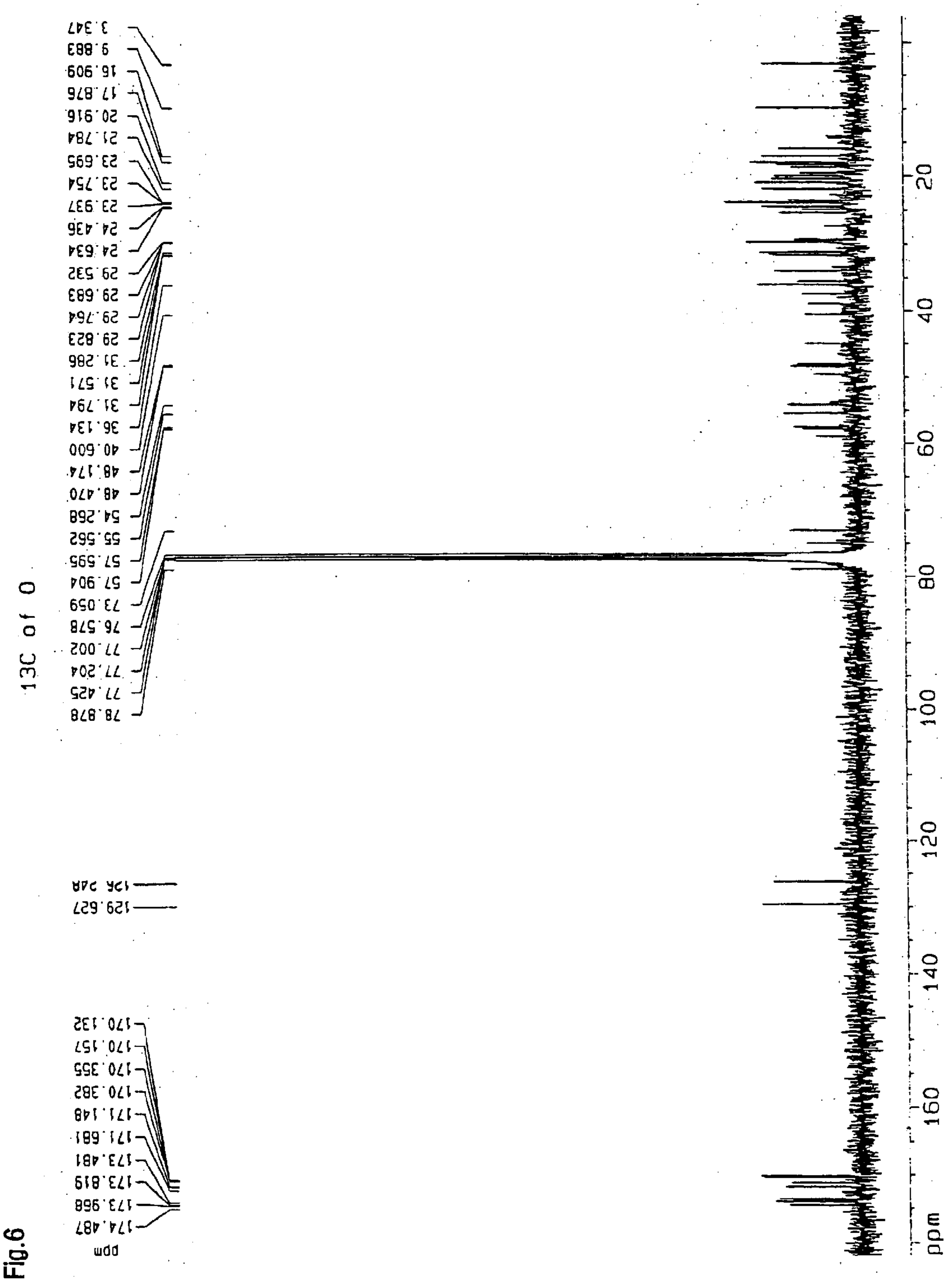
FIG. 6 is a $^{13}$C-NMR spectrum of [D-2-(methylamino) hexa-4-ynoyl$^3$] cyclosporin A.

According to the general method, to a solution of 10 equivalents of LDA was added 1.0 g cyclosporin A in 50 ml THF at −78° C. The reaction mixture was stirred for 2 hrs at −78° C. and added with 0.73 ml 1-bromo-2-butyne. After the temperature of the solution reached room temperature, the solution was further stirred for 24 hrs and added with 20 ml water, followed by concentration. The residue was added with ether ($Et_2O$), washed with water and a solution of saturated sodium chloride in sequence, and dried over anhydrous $MgSO_4$. After concentrating, the residue was subjected to silica gel column chromatography (100 g silica gel, dichloromethane:methylalcohol=96:4), followed by HPLC to give 0.13 g of the title compound. Molecular weight of the compound was determined by FAB MS (ZMS AX 505H) analysis. To confirm the molecular structure, Nuclear Magnetic Resonance (NMR) measurements were performed on 600 MHz (Bruker) for $^1$H-NMR and on 150 MHz (Bruker) for $^{13}$C-NMR, and the spectra are shown in FIGS. 5 and 6, respectively.

1–4: Synthesis of [D-2-(methylamino)pent-4-ynoyl$^3$] cyclosporin A: Compound 4

Figure 7:
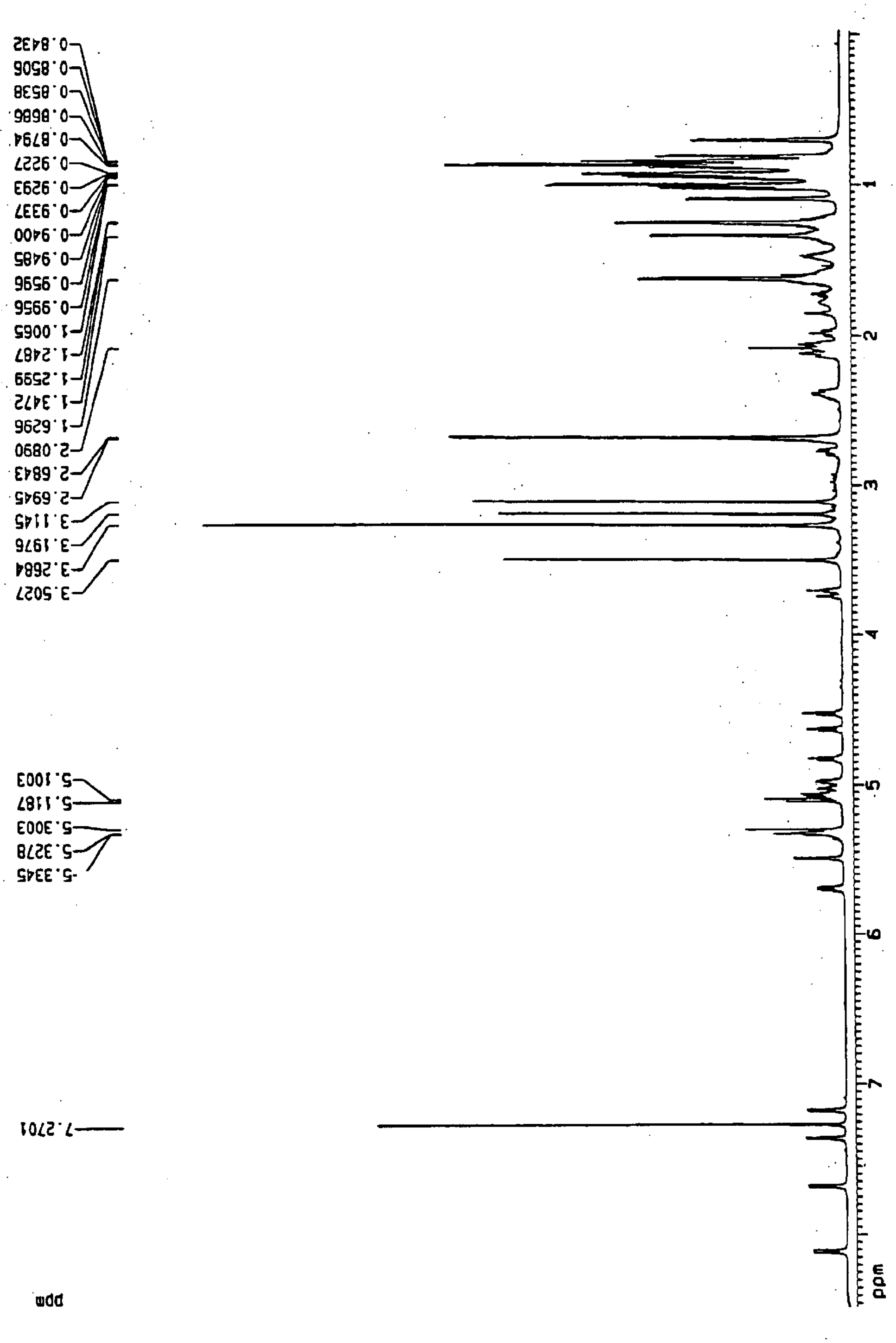
FIG. 7 is a $^1$H-NMR spectrum of [D-2-(methylamino) pent-4-ynoyl$^3$] cyclosporin A.
Figure 8:
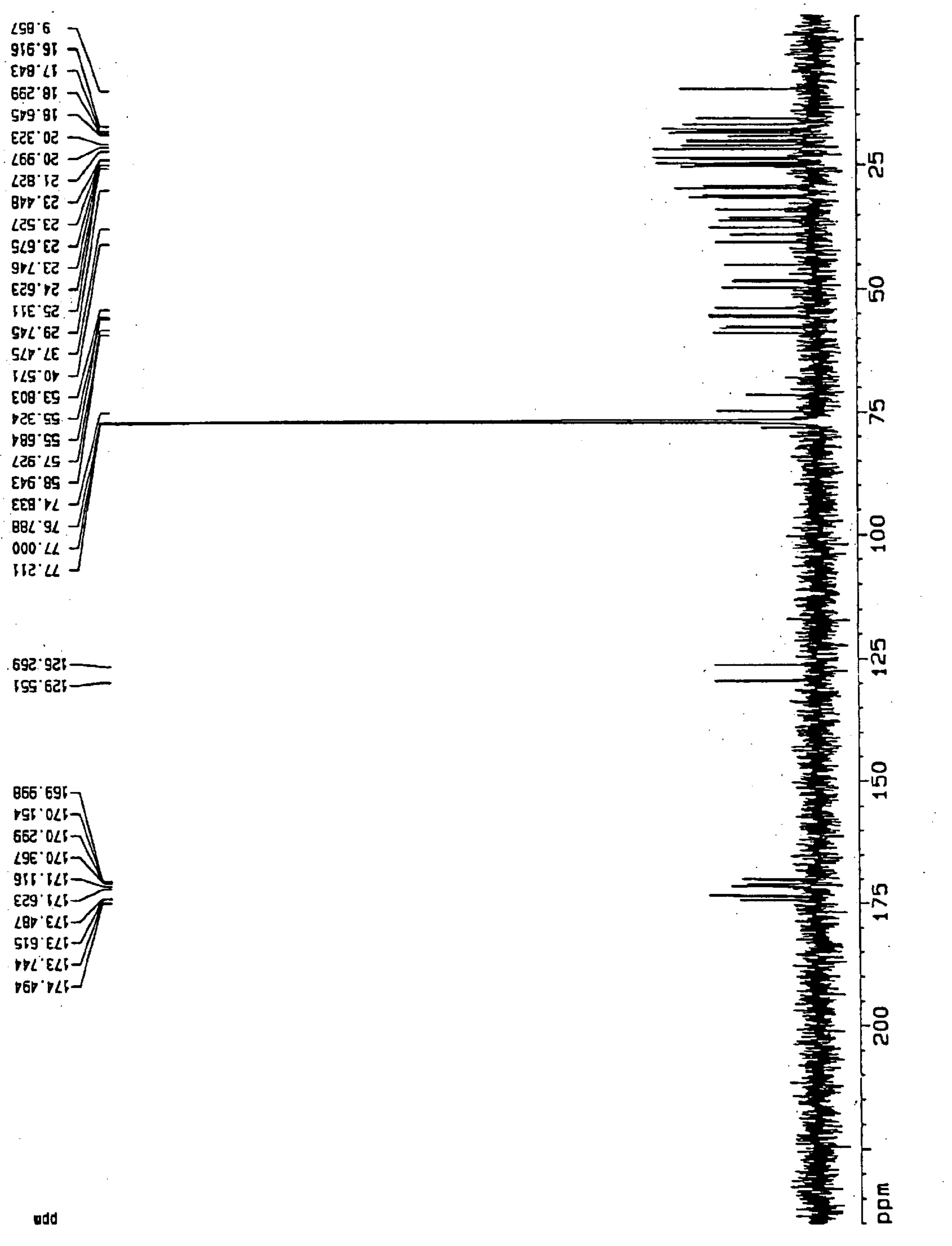
FIG. 8 is a $^{13}$C-NMR spectrum of [D-2-(methylamino) pent-4-ynoyl$^3$] cyclosporin A.

According to the general method, alkylation was performed employing THF (200 ml), $(i\text{-}Pr)_2NH$ (3.2 ml), BuLi (8 ml), cyclosporin A (3.76 g) in 50 ml THF and propargyl bromide (3.57 g). After the temperature of the solution reached room temperature, the solution was further stirred for 24 hrs and added with 40 ml water, followed by concentration. The residue was added with ether ($Et_2O$), washed with water and a solution of saturated sodium chloride in sequence, and dried over anhydrous $MgSO_4$. After concentrating, the residue was subjected to silica gel column chromatography (100 g silica gel, dichloromethane:methylalcohol=96:4), followed by HPLC to give the title compounds 3 (0.18 g) and 4 (0.08 g). Molecular weight of the compound was determined by FAB MS (ZMS AX 505H) analysis. To confirm the molecular structure, Nuclear Magnetic Resonance (NMR) measurements were performed on 600 MHz (Bruker) for $^1$H-NMR and on 150 MHz (Bruker) for $^{13}$C-NMR, and the spectra are shown in FIGS. 7 and 8, respectively.

1–5: Synthesis of [D-2-(methylthio)-Sar$^3$] cyclosporin A: Compound 5

Figure 9:
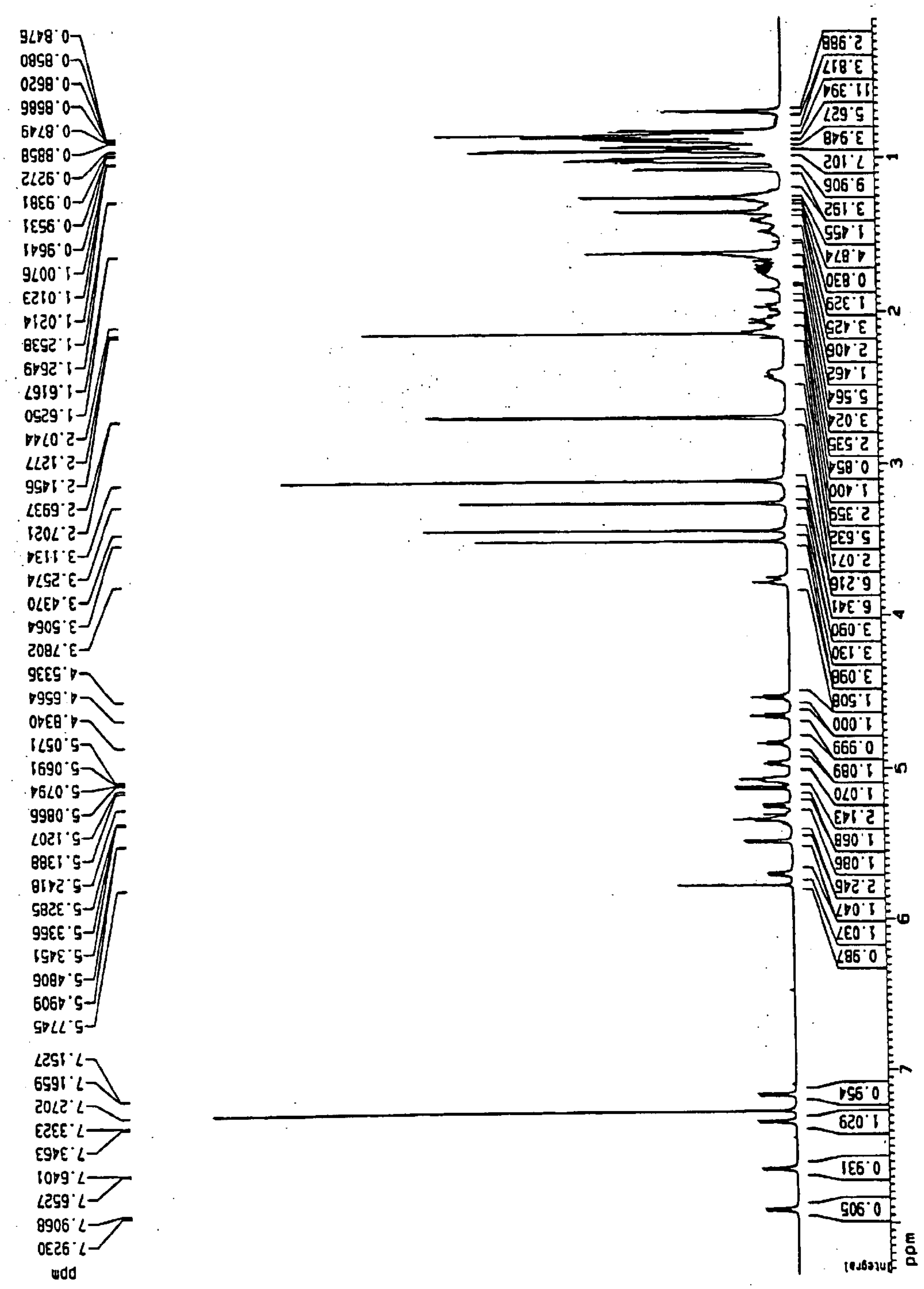
FIG. 9 is a $^1$H-NMR spectrum of [D-2-(methylthio)-Sar$^3$] cyclosporin A.
Figure 10:
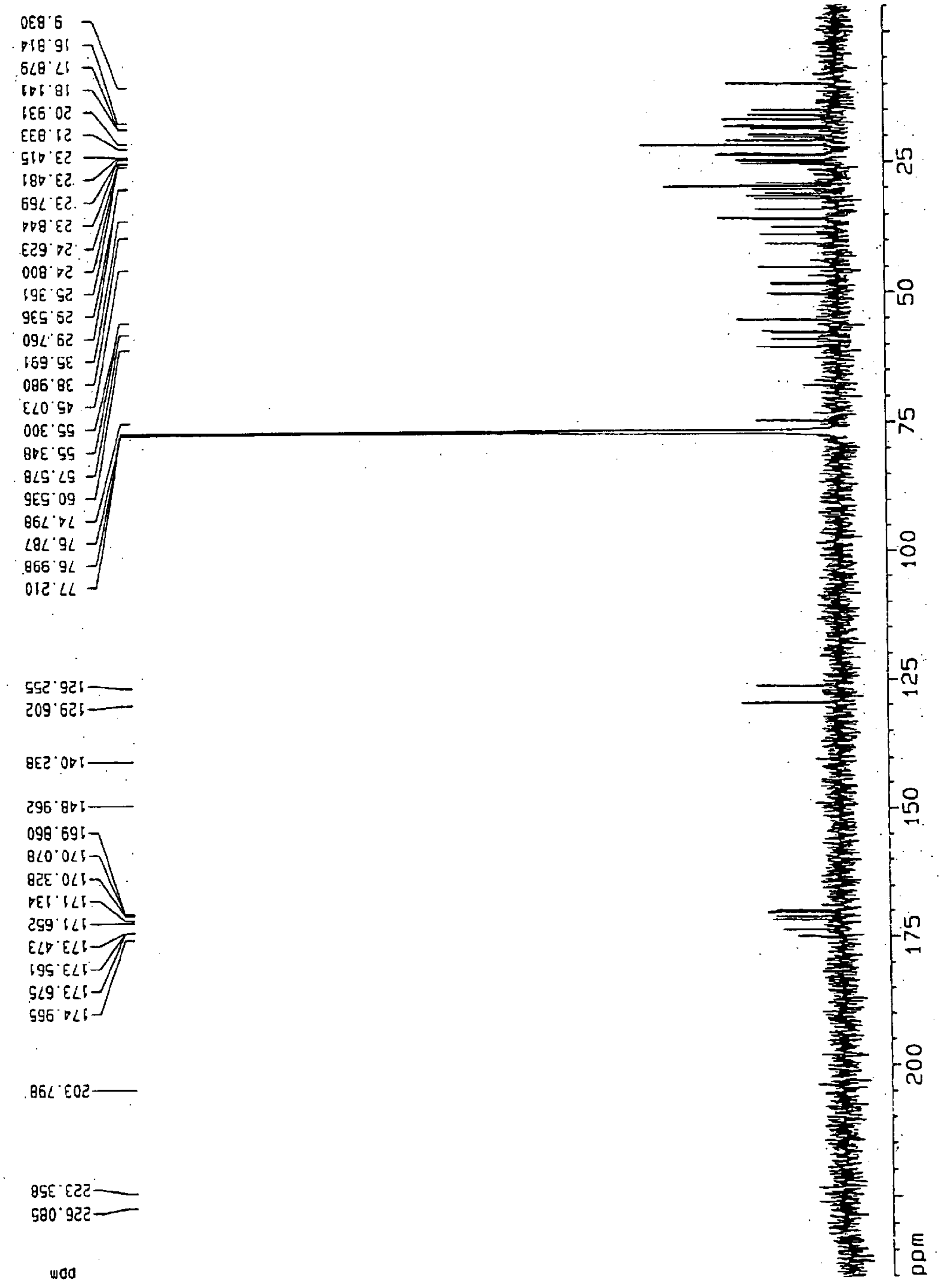
FIG. 10 is a $^{13}$C-NMR spectrum of [D-2-(methylthio)-Sar$^3$] cyclosporin A.

According to the general method, alkylation was performed employing THF (100 ml), $(i\text{-}Pr)_2NH$ (1.6 ml), BuLi (4.0 ml), cyclosporin A (1.0 g) in 30 ml THF and methyl disulfide ($Me_2S_2$) (1.5 ml). The solution was stirred for 14 hrs at 0° C. and added with 20 ml water, followed by concentration. The residue was added with ether ($Et_2O$), washed with water and a solution of saturated sodium chloride in sequence, and dried over anhydrous $MgSO_4$. After concentrating, the residue was subjected to silica gel column chromatography (100 g silica gel, dichloromethane:methylalcohol=50:1~96:4), followed by HPLC to give the title compounds 5 (0.36 g) and 6 (0.05 g). Molecular weight of the compound was determined by FAB MS (ZMS AX 505H) analysis. To confirm the molecular structure, Nuclear Magnetic Resonance (NMR) measurements were performed on 600 MHz (Bruker) for $^1$H-NMR and on 150 MHz (Bruker) for $^{13}$C-NMR, and the spectra are shown in FIGS. 9 and 10, respectively.

1–6: Synthesis of [N-methyl-O-propenyl-D-Ser$^3$] cyclosporin A: Compound 6

Figure 11:
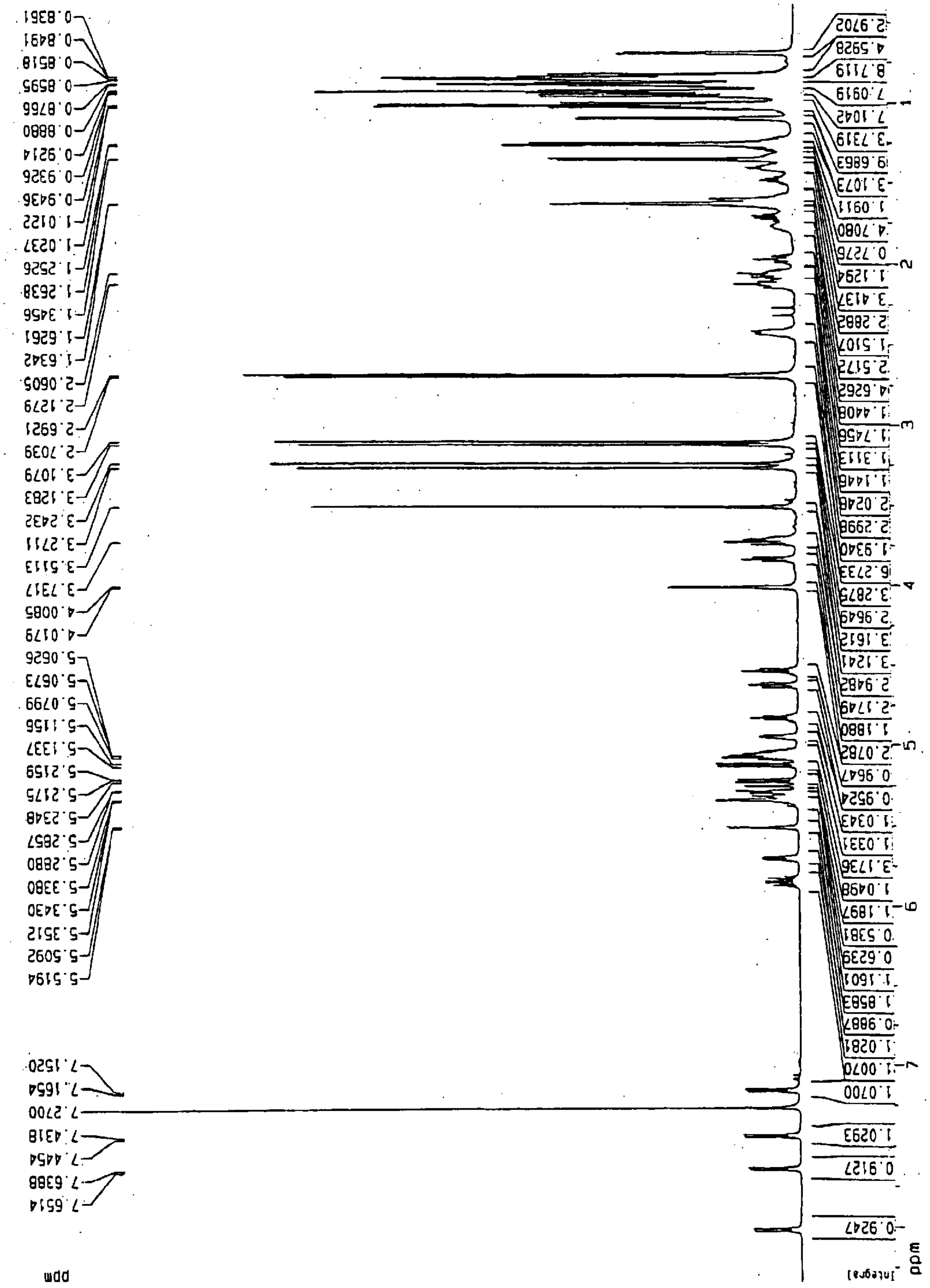
FIG. 11 is a $^1$H-NMR spectrum of [N-methyl-O-propenyl-D-Ser$^3$] cyclosporin A.
Figure 12:
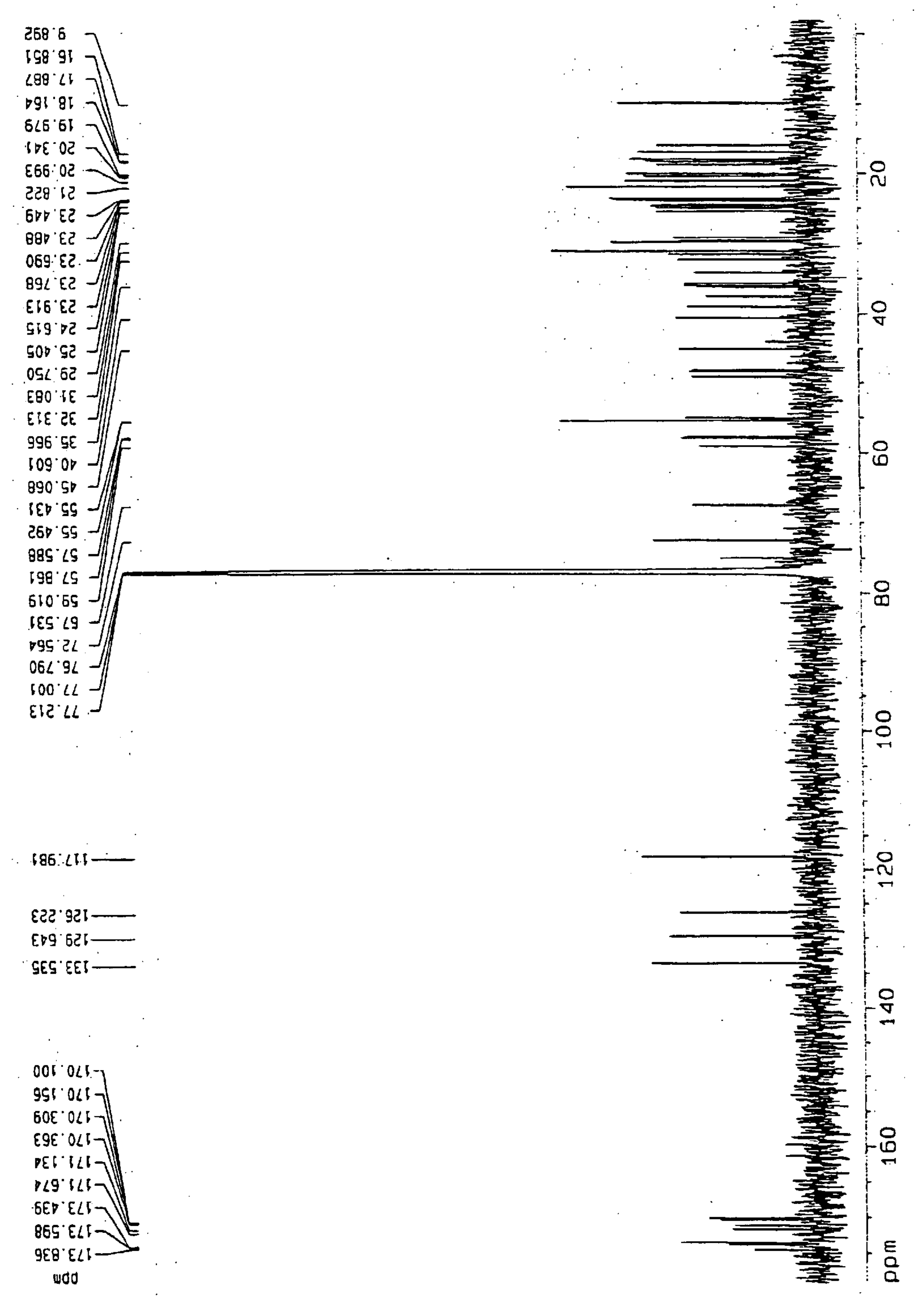
FIG. 12 is a $^{13}$C-NMR spectrum of [N-methyl-O-propenyl-D-Ser$^3$] cyclosporin A.

According to the general method, [D-methylserine$^3$] cyclosporin A (0.62 g, 0.5 mmol), tetrabutylammonium chloride (0.11 g, 0.5 mmol), and aryl bromide (0.24 g, 2.0 mmol) were dissolved in dichloromethane (50 ml), then added with 30% NaOH (1.5 ml), and the mixture was stirred for 2 hrs. After adding with 50 ml dichloromethane, the solution was washed with water and a solution of saturated sodium chloride in sequence, and dried over anhydrous $MgSO_4$. The concentrated residue was subjected to silica gel column chromatography (100 g silica gel, dichloromethane:methylalcohol=97:3), followed by HPLC to give 0.4 g of the title compound. Molecular weight of the compound was determined by FAB MS (ZMS AX 505H) analysis. To confirm the molecular structure, Nuclear Magnetic Resonance (NMR) measurements were performed on 600 MHz (Bruker) for $^1$H-NMR and on 150 MHz (Bruker) for $^{13}$C-NMR, and the spectra are shown in FIGS. 11 and 12, respectively.

1–7: Synthesis of [N-methyl-D-Ser$^3$] cyclosporin A: Compound 7

Figure 13:
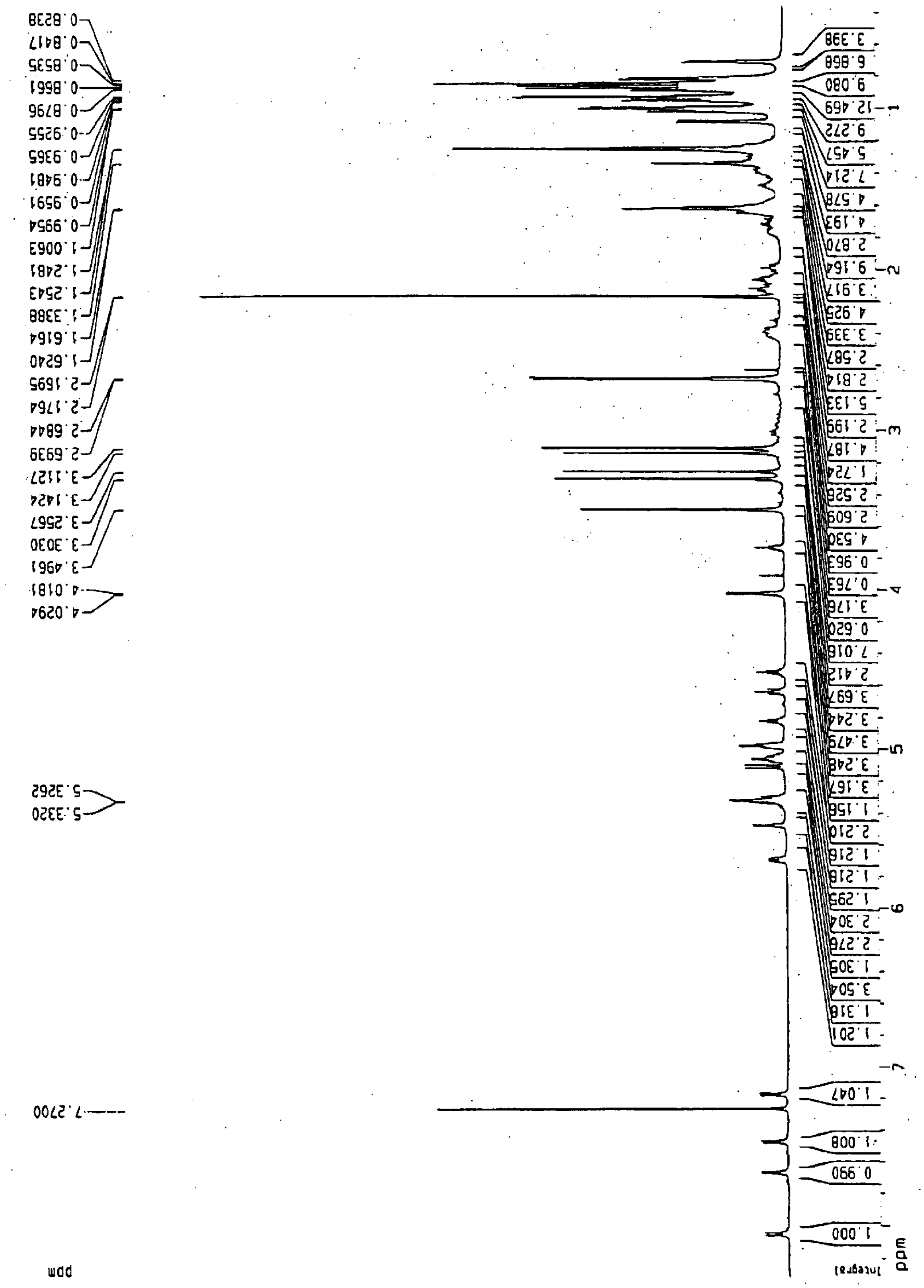
FIG. 13 is a $^1$H-NMR spectrum of [N-methyl-D-Ser$^3$] cyclosporin A.
Figure 14:
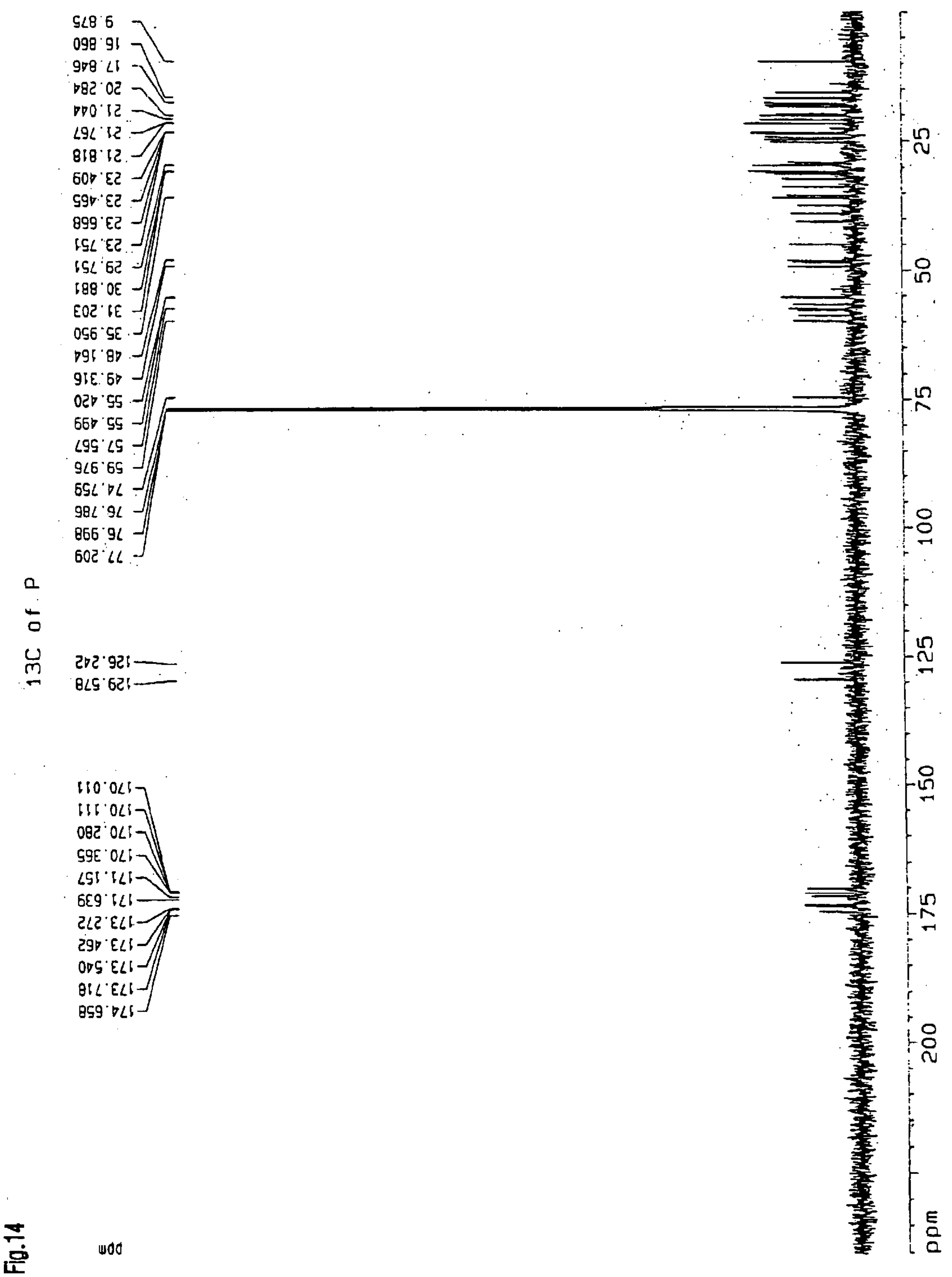
FIG. 14 is a $^{13}$C-NMR spectrum of [N-methyl-D-Ser$^3$] cyclosporin A.

According to the general method, to a solution of 10 equivalents of LDA was added 1.0 g cyclosporin A in 50 ml THF at −78° C. The reaction mixture was stirred for 2 hrs at −78° C. and added with 2.0 g paraformaldehyde. After the temperature of the solution reached room temperature, the solution was further stirred for 24 hrs and added with 20 ml water, followed by concentration. The residue was added with ether ($Et_2O$), washed with water and a solution of saturated sodium chloride in sequence, and dried over anhydrous $MgSO_4$. After concentrating, the residue was subjected to silica gel column chromatography (100 g silica gel, dichloromethane:methylalcohol=96:4), followed by HPLC to give 0.3 g of the title compound. Molecular weight of the compound was determined by FAB MS (ZMS AX 505H) analysis. To confirm the molecular structure, Nuclear Magnetic Resonance (NMR) measurements were performed on 600 MHz (Bruker) for $^1$H-NMR and on 150 MHz (Bruker) for $^{13}$C-NMR, and the spectra are shown in FIGS. 13 and 14, respectively.

PREPARATIVE EXAMPLE 1

Hair Tonic

1–1: Preparation of Hair Tonic Containing [N-methyl-D-Abu$^3$] Cyclosporin A

Individual ingredients were mixed and stirred, and the mixtures were completely dissolved to prepare three hair growth promoting tonics, with compositions as shown in Table 1 below. It was found that the composition 1 of Table 1 has a hair growth promoting effect at a level similar to a conventional hair tonic containing 0.1% cyclosporin A, as evaluated in an animal experiment according to the Test Example described later.

TABLE 1

| Formulation of hair tonic | | | |
|---|---|---|---|
| | (unit: weight %) | | |
| Ingredients | Comp. 1 | Comp. 2 | Comp. 3 |
| ethanol | 40.0 | 40.0 | 40.0 |
| [N-methyl-D-Abu$^3$] cyclosporin A | 0.1 | 1.0 | 8.0 |
| tocopherol acetate | 0.1 | 0.1 | 0.1 |
| salicylic acid | 0.3 | 0.3 | 0.3 |
| L-menthol | 0.3 | 0.3 | 0.3 |
| Tween 20 | 0.5 | 0.5 | 0.5 |
| flavor | typical | typical | typical |
| colarant | typical | typical | typical |
| water | balance | balance | balance |

1–2: Preparation of Hair Tonic Containing [N-methyl-D-Nva$^3$] Cyclosporin A

Individual ingredients were mixed and stirred, and the mixtures were completely dissolved to prepare three hair growth promoting tonics, with compositions as shown in Table 2 below. It was found that the composition 1 of Table 2 has a hair growth promoting effect at a level similar to a conventional hair tonic containing 0.1% cyclosporin A, as evaluated in an animal experiment according to the Test Example described later.

TABLE 2

| Formulation of hair tonic | | | |
|---|---|---|---|
| | (unit: weight %) | | |
| Ingredients | Comp. 1 | Comp. 2 | Comp. 3 |
| ethanol | 40.0 | 40.0 | 40.0 |
| [N-methyl-D-Nva$^3$] cyclosporin A | 0.1 | 1.0 | 8.0 |
| tocopherol acetate | 0.1 | 0.1 | 0.1 |
| salicylic acid | 0.3 | 0.3 | 0.3 |
| L-menthol | 0.3 | 0.3 | 0.3 |
| Tween 20 | 0.5 | 0.5 | 0.5 |
| flavor | typical | typical | typical |
| colarant | typical | typical | typical |
| water | balance | balance | balance |

1–3: Preparation of Hair Tonic Containing [D-2-(methylamino)hexa-4-ynoyl$^3$] Cyclosporin A Individual ingredients were mixed and stirred, and the mixtures were completely dissolved to prepare three hair growth promoting tonics, with compositions as shown in Table 3 below. It was found that the composition 1 of Table 3 has a hair growth promoting effect at a level similar to a conventional hair tonic containing 0.1% cyclosporin A, as evaluated in an animal experiment according to the Test Example described later.

TABLE 3

| Formulation of hair tonic | | | |
|---|---|---|---|
| | (unit: weight %) | | |
| Ingredients | Comp. 1 | Comp. 2 | Comp. 3 |
| ethanol | 40.0 | 40.0 | 40.0 |
| [D-2-(methylamino)hexa-4-ynoyl$^3$] cyclosporin A | 0.1 | 1.0 | 8.0 |
| tocopherol acetate | 0.1 | 0.1 | 0.1 |
| salicylic acid | 0.3 | 0.3 | 0.3 |
| L-menthol | 0.3 | 0.3 | 0.3 |
| Tween 20 | 0.5 | 0.5 | 0.5 |

TABLE 3-continued

| Formulation of hair tonic | | | |
|---|---|---|---|
| | (unit: weight %) | | |
| Ingredients | Comp. 1 | Comp. 2 | Comp. 3 |
| flavor | typical | typical | typical |
| colarant | typical | typical | typical |
| water | balance | balance | balance |

1–4: Preparation of Hair Tonic Containing [D-2-(methylamino)pent-4-ynoyl$^3$] Cyclosporin A Individual ingredients were mixed and stirred, and the mixtures were completely dissolved to prepare three hair growth promoting tonics, with compositions as shown in Table 4 below. It was found that the composition 1 of Table 4 has a hair growth promoting effect at a level similar to a conventional hair tonic containing 0.1% cyclosporin A, as evaluated in an animal experiment according to the Test Example described later.

TABLE 4

| Formulation of hair tonic | | | |
|---|---|---|---|
| | (unit: weight %) | | |
| Ingredients | Comp. 1 | Comp. 2 | Comp. 3 |
| ethanol | 40.0 | 40.0 | 40.0 |
| [D-2-(methylamino)pent-4-ynoyl$^3$] cyclosporin A | 0.1 | 1.0 | 8.0 |
| tocopherol acetate | 0.1 | 0.1 | 0.1 |
| salicylic acid | 0.3 | 0.3 | 0.3 |
| L-menthol | 0.3 | 0.3 | 0.3 |
| Tween 20 | 0.5 | 0.5 | 0.5 |
| flavor | typical | typical | typical |
| colarant | typical | typical | typical |
| water | balance | balance | balance |

1–5: Preparation of Hair Tonic Containing [D-2-methylthio-Sar$^3$] Cyclosporin A Individual ingredients were mixed and stirred, and the mixtures were completely dissolved to prepare three hair growth promoting tonics, with compositions as shown in Table 5 below. It was found that the composition 1 of Table 5 has a hair growth promoting effect at a level similar to a conventional hair tonic containing 0.1% cyclosporin A, as evaluated in an animal experiment according to the Test Example described later.

TABLE 5

| Formulation of hair tonic | | | |
|---|---|---|---|
| | (unit: weight %) | | |
| Ingredients | Comp. 1 | Comp. 2 | Comp. 3 |
| ethanol | 40.0 | 40.0 | 40.0 |
| [D-2-(methylthio)-Sar$^3$] cyclosporin A | 0.1 | 1.0 | 8.0 |
| tocopherol acetate | 0.1 | 0.1 | 0.1 |
| salicylic acid | 0.3 | 0.3 | 0.3 |
| L-menthol | 0.3 | 0.3 | 0.3 |
| Tween 20 | 0.5 | 0.5 | 0.5 |
| flavor | typical | typical | typical |
| colarant | typical | typical | typical |
| water | balance | balance | balance |

1–6: Preparation of Hair Tonic Containing [N-methyl-O-propenyl-D-Ser$^3$] Cyclosporin A Individual ingredients were mixed and stirred, and the mixtures were completely dissolved to prepare three hair growth promoting tonics, with compositions as shown in Table 6 below. It was found that the composition 1 of Table 6 has a hair growth promoting effect at a level similar to a conventional hair tonic containing 0.1% cyclosporin A, as evaluated in an animal experiment according to the Test Example described later.

TABLE 6

Formulation of hair tonic

| Ingredients | Comp. 1 | Comp. 2 | Comp. 3 |
|---|---|---|---|
| | (unit: weight %) | | |
| ethanol | 40.0 | 40.0 | 40.0 |
| [N-methyl-O-propenyl-D-Ser$^3$] cyclosporin A | 0.1 | 1.0 | 8.0 |
| tocopherol acetate | 0.1 | 0.1 | 0.1 |
| salicylic acid | 0.3 | 0.3 | 0.3 |
| L-menthol | 0.3 | 0.3 | 0.3 |
| Tween 20 | 0.5 | 0.5 | 0.5 |
| flavor | typical | typical | typical |
| colarant | typical | typical | typical |
| water | balance | balance | balance |

1–7: Preparation of Hair Tonic Containing [N-methyl-D-Ser$^3$] Cyclosporin A

Individual ingredients were mixed and stirred, and the mixtures were completely dissolved to prepare three hair growth promoting tonics, with compositions as shown in Table 7 below. It was found that the composition 1 of Table 7 has a hair growth promoting effect at a level similar to a conventional hair tonic containing 0.1% cyclosporin A, as evaluated in an animal experiment according to the Test Example described later.

TABLE 7

Formulation of hair tonic

| Ingredients | Comp. 1 | Comp. 2 | Comp. 3 |
|---|---|---|---|
| | (unit: weight %) | | |
| ethanol | 40.0 | 40.0 | 40.0 |
| [N-methyl-D-Ser$^3$] cyclosporin A | 0.1 | 1.0 | 8.0 |
| tocopherol acetate | 0.1 | 0.1 | 0.1 |
| salicylic acid | 0.3 | 0.3 | 0.3 |
| L-menthol | 0.3 | 0.3 | 0.3 |
| Tween 20 | 0.5 | 0.5 | 0.5 |
| flavor | typical | typical | typical |
| colarant | typical | typical | typical |
| water | balance | balance | balance |

PREPARATIVE EXAMPLE 2

Hair Cream

2–1: Preparation of Hair Cream Containing [N-methyl-D-Abu$^3$] Cyclosporin A

Individual oil-phase and water-phase ingredients were mixed in a separate container, and each mixture was completely dissolved by heating to 80° C. Two phases of the ingredients were mixed, emulsified, and cooled to room temperature. Additives such as flavor and colorant were admixed to prepare three hair creams, with compositions as shown in Table 8 below. Water was added to adjust to 100% the total weight including the oil-phase and water-phase ingredients.

It was found that the composition 1 of Table 8 has a hair growth promoting effect at a level similar to a conventional hair cream containing 0.1% cyclosporin A, as evaluated in an animal experiment according to the Test Example described later.

TABLE 8

Formulation of hair cream

| Ingredients | Comp. 1 | Comp. 2 | Comp. 3 |
|---|---|---|---|
| | (unit: weight %) | | |
| paraffin | 5.0 | 5.0 | 5.0 |
| cetostearyl alcohol | 5.5 | 5.5 | 5.5 |
| petrolatum | 5.5 | 5.5 | 5.5 |
| glycerin monostearate | 3.0 | 3.0 | 3.0 |
| polyoxyethyleneoctyldodecylether | 3.0 | 3.0 | 3.0 |
| propylparaben | 0.3 | 0.3 | 0.3 |
| [N-methyl-D-Abu$^3$] cyclosporin A | 0.1 | 1.0 | 8.0 |
| glycerin | 7.0 | 7.0 | 7.0 |
| dipropyleneglycol | 20.0 | 20.0 | 20.0 |
| polyethyleneglycol | 5.0 | 5.0 | 5.0 |
| water | balance not including flavor and colorant | | |
| flavor | typical | typical | typical |
| colorant | typical | typical | typical |

2–2: Preparation of Hair Cream Containing [N-methyl-D-Nva$^3$] Cyclosporin A

Individual oil-phase and water-phase ingredients were mixed in a separate container, and each mixture was completely dissolved by heating to 80° C. Two phases of the ingredients were mixed, emulsified, and cooled to room temperature. Additives such as flavor and colorant were admixed to prepare three hair creams, with compositions as shown in Table 9 below. Water was added to adjust to 100% the total weight including the oil-phase and water-phase ingredients.

It was found that the composition 1 of Table 9 has a hair growth promoting effect at a level similar to a conventional hair cream containing 0.1% cyclosporin A, as evaluated in an animal experiment according to the Test Example described later.

TABLE 9

Formulation of hair cream

| Ingredients | Comp. 1 | Comp. 2 | Comp. 3 |
|---|---|---|---|
| | (unit: weight %) | | |
| paraffin | 5.0 | 5.0 | 5.0 |
| cetostearyl alcohol | 5.5 | 5.5 | 5.5 |
| petrolatum | 5.5 | 5.5 | 5.5 |
| glycerin monostearate | 3.0 | 3.0 | 3.0 |
| polyoxyethyleneoctyldodecylether | 3.0 | 3.0 | 3.0 |
| propylparaben | 0.3 | 0.3 | 0.3 |
| [N-methyl-D-Nva$^3$] cyclosporin A | 0.1 | 1.0 | 8.0 |
| glycerin | 7.0 | 7.0 | 7.0 |
| dipropyleneglycol | 20.0 | 20.0 | 20.0 |
| polyethyleneglycol | 5.0 | 5.0 | 5.0 |
| water | balance not including flavor and colorant | | |
| flavor | typical | typical | typical |
| colorant | typical | typical | typical |

2–3: Preparation of Hair Cream Containing [D-2-(methylamino)hexa-4-ynoyl$^3$] Cyclosporin A Individual oil-phase and water-phase ingredients were mixed in a separate container, and each mixture was completely dissolved by heating to 80° C. Two phases of the ingredients were mixed, emulsified, and cooled to room temperature. Additives such as flavor and colorant were admixed to prepare three hair creams, with compositions as shown in Table 10 below. Water was added to adjust to 100% the total weight including the oil-phase and water-phase ingredients.

It was found that the composition 1 of Table 10 has a hair growth promoting effect at a level similar to a conventional hair cream containing 0.1% cyclosporin A, as evaluated in an animal experiment according to the Test Example described later.

TABLE 10

Formulation of hair cream

| Ingredients | (unit: weight %) Comp. 1 | Comp. 2 | Comp. 3 |
|---|---|---|---|
| paraffin | 5.0 | 5.0 | 5.0 |
| cetostearyl alcohol | 5.5 | 5.5 | 5.5 |
| petrolatum | 5.5 | 5.5 | 5.5 |
| glycerin monostearate | 3.0 | 3.0 | 3.0 |
| polyoxyethyleneoctyldodecylether | 3.0 | 3.0 | 3.0 |
| propylparaben | 0.3 | 0.3 | 0.3 |
| [D-2-(methylamino)hexa-4-ynoyl$^3$]cyclosporin A | 0.1 | 1.0 | 8.0 |
| glycerin | 7.0 | 7.0 | 7.0 |
| dipropyleneglycol | 20.0 | 20.0 | 20.0 |
| polyethyleneglycol | 5.0 | 5.0 | 5.0 |
| water | balance not including flavor and colorant | | |
| flavor | typical | typical | typical |
| colorant | typical | typical | typical |

2–4: Preparation of Hair Cream Containing [D-2-(methylamino)pent-4-ynoyl$^3$] Cyclosporin A Individual oil-phase and water-phase ingredients were mixed in a separate container, and each mixture was completely dissolved by heating to 80° C. Two phases of the ingredients were mixed, emulsified, and cooled to room temperature. Additives such as flavor and colorant were admixed to prepare three hair creams, with compositions as shown in Table 11 below. Water was added to adjust to 100% the total weight including the oil-phase and water-phase ingredients.

It was found that the composition 1 of Table 11 has a hair growth promoting effect at a level similar to a conventional hair cream containing 0.1% cyclosporin A, as evaluated in an animal experiment according to the Test Example described later.

TABLE 11

Formulation of hair cream

| Ingredients | (unit: weight %) Comp. 1 | Comp. 2 | Comp. 3 |
|---|---|---|---|
| paraffin | 5.0 | 5.0 | 5.0 |
| cetostearyl alcohol | 5.5 | 5.5 | 5.5 |
| petrolatum | 5.5 | 5.5 | 5.5 |
| glycerin monostearate | 3.0 | 3.0 | 3.0 |
| polyoxyethyleneoctyldodecylether | 3.0 | 3.0 | 3.0 |
| propylparaben | 0.3 | 0.3 | 0.3 |
| [D-2-(methylamino)pent-4-ynoyl$^3$] cyclosporin A | 0.1 | 1.0 | 8.0 |

TABLE 11-continued

Formulation of hair cream

| Ingredients | (unit: weight %) Comp. 1 | Comp. 2 | Comp. 3 |
|---|---|---|---|
| glycerin | 7.0 | 7.0 | 7.0 |
| dipropyleneglycol | 20.0 | 20.0 | 20.0 |
| polyethyleneglycol | 5.0 | 5.0 | 5.0 |
| water | balance not including flavor and colorant | | |
| flavor | typical | typical | typical |
| colorant | typical | typical | typical |

2–5: Preparation of Hair Cream Containing [D-2-methylthio-Sar$^3$] Cyclosporin A Individual oil-phase and water-phase ingredients were mixed in a separate container, and each mixture was completely dissolved by heating to 80° C. Two phases of the ingredients were mixed, emulsified, and cooled to room temperature. Additives such as flavor and colorant were admixed to prepare three hair creams, with compositions as shown in Table 12 below. Water was added to adjust to 100% the total weight including the oil-phase and water-phase ingredients.

It was found that the composition 1 of Table 12 has a hair growth promoting effect at a level similar to a conventional hair cream containing 0.1% cyclosporin A, as evaluated in an animal experiment according to the Test Example described later.

TABLE 12

Formulation of hair cream

| Ingredients | (unit: weight %) Comp. 1 | Comp. 2 | Comp. 3 |
|---|---|---|---|
| paraffin | 5.0 | 5.0 | 5.0 |
| cetostearyl alcohol | 5.5 | 5.5 | 5.5 |
| petrolatum | 5.5 | 5.5 | 5.5 |
| glycerin monostearate | 3.0 | 3.0 | 3.0 |
| polyoxyethyleneoctyldodecylether | 3.0 | 3.0 | 3.0 |
| propylparaben | 0.3 | 0.3 | 0.3 |
| [D-2-methylthio-Sar$^3$] cyclosporin A | 0.1 | 1.0 | 8.0 |
| glycerin | 7.0 | 7.0 | 7.0 |
| dipropyleneglycol | 20.0 | 20.0 | 20.0 |
| polyethyleneglycol | 5.0 | 5.0 | 5.0 |
| water | balance not including flavor and colorant | | |
| flavor | typical | typical | typical |
| colorant | typical | typical | typical |

2–6: Preparation of Hair Cream Containing [N-methyl-O-propenyl-D-Ser$^3$] Cyclosporin A Individual oil-phase and water-phase ingredients were mixed in a separate container, and each mixture was completely dissolved by heating to 80° C. Two phases of the ingredients were mixed, emulsified, and cooled to room temperature. Additives such as flavor and colorant were admixed to prepare three hair creams, with compositions as shown in Table 13 below. Water was added to adjust to 100% the total weight including the oil-phase and water-phase ingredients.

It was found that the composition 1 of Table 13 has a hair growth promoting effect at a level similar to a conventional hair cream containing 0.1% cyclosporin A, as evaluated in an animal experiment according to the Test Example described later.

TABLE 13

| Formulation of hair cream | | | |
|---|---|---|---|
| | (unit: weight %) | | |
| Ingredients | Comp. 1 | Comp. 2 | Comp. 3 |
| paraffin | 5.0 | 5.0 | 5.0 |
| cetostearyl alcohol | 5.5 | 5.5 | 5.5 |
| petrolatum | 5.5 | 5.5 | 5.5 |
| glycerin monostearate | 3.0 | 3.0 | 3.0 |
| polyoxyethyleneoctyldodecylether | 3.0 | 3.0 | 3.0 |
| propylparaben | 0.3 | 0.3 | 0.3 |
| [N-methyl-O-propenyl-D-$Ser^3$] cyclosporin A | 0.1 | 1.0 | 8.0 |
| glycerin | 7.0 | 7.0 | 7.0 |
| dipropyleneglycol | 20.0 | 20.0 | 20.0 |
| polyethyleneglycol | 5.0 | 5.0 | 5.0 |
| water | balance not including flavor and colorant | | |
| flavor | typical | typical | typical |
| colorant | typical | typical | typical |

2–7: Preparation of Hair Cream Containing [N-methyl-D-$Ser^3$] Cyclosporin A

Individual oil-phase and water-phase ingredients were mixed in a separate container, and each mixture was completely dissolved by heating to 80° C. Two phases of the ingredients were mixed, emulsified, and cooled to room temperature. Additives such as flavor and colorant were admixed to prepare three hair cream, with compositions as shown in Table 14 below. Water was added to adjust to 100% the total weight including the oil-phase and water-phase ingredients.

It was found that the composition 1 of Table 14 has a hair growth promoting effect at a level similar to a conventional hair cream containing 0.1% cyclosporin A, as evaluated in an animal experiment according to the Test Example described later.

TABLE 14

| Formulation of hair cream | | | |
|---|---|---|---|
| | (unit: weight %) | | |
| Ingredients | Comp. 1 | Comp. 2 | Comp. 3 |
| paraffin | 5.0 | 5.0 | 5.0 |
| cetostearyl alcohol | 5.5 | 5.5 | 5.5 |
| petrolatum | 5.5 | 5.5 | 5.5 |
| glycerin monostearate | 3.0 | 3.0 | 3.0 |
| polyoxyethyleneoctyldodecylether | 3.0 | 3.0 | 3.0 |
| propylparaben | 0.3 | 0.3 | 0.3 |
| [N-methy-D-$Ser^3$] cyclosporin A | 0.1 | 1.0 | 8.0 |
| glycerin | 7.0 | 7.0 | 7.0 |
| dipropyleneglycol | 20.0 | 20.0 | 20.0 |
| polyethyleneglycol | 5.0 | 5.0 | 5.0 |
| water | balance not including flavor and colorant | | |
| flavor | typical | typical | typical |
| colorant | typical | typical | typical |

PREPARATIVE EXAMPLE 3

Shampoo

3–1: Preparation of Shampoo Containing [N-methyl-D-$Abu^3$] Cyclosporin A

All individual ingredients, except flavor, colorant and water, were mixed and the mixture was completely dissolved by heating, while stirring. After cooling to room temperature, the mixture was mixed with flavor and colorant. Water was finally added to adjust to 100% the total weight, to prepare three shampoos, with compositions as shown in Table 15 below.

TABLE 15

| Formulation of shampoo | | | |
|---|---|---|---|
| | (unit: weight %) | | |
| Ingredients | Comp. 1 | Comp. 2 | Comp. 3 |
| sodium POE laurylsulfuric acid (30 wt % aqueous solution) | 40.0 | 40.0 | 40.0 |
| palm oil fattyacid diethanolamide | 3.0 | 3.0 | 3.0 |
| propyleneglycol | 2.0 | 2.0 | 2.0 |
| methyl paraoxybenzoic acid | 0.2 | 0.2 | 0.2 |
| ehtanol | 2.0 | 2.0 | 2.0 |
| [N-methyl-D-$Abu^3$] cyclosporin A | 1.0 | 3.0 | 10.0 |
| salicylic acid | 0.3 | 0.3 | 0.3 |
| L-menthol | 0.3 | 0.3 | 0.3 |
| flavor | typical | typical | typical |
| colorant | typical | typical | typical |
| water | balance | balance | balance |

3–2: Preparation of Shampoo Containing [N-methyl-D-$Nva^3$] Cyclosporin A

All individual ingredients, except flavor, colorant and water, were mixed and the mixture was completely dissolved by heating, while stirring. After cooling to room temperature, the mixture was mixed with flavor and colorant. Water was finally added to adjust to 100% the total weight, to prepare three shampoos, with compositions as shown in Table 16 below.

TABLE 16

| Formulation of shampoo | | | |
|---|---|---|---|
| | (unit: weight %) | | |
| Ingredients | Comp. 1 | Comp. 2 | Comp. 3 |
| sodium POE laurylsulfuric acid (30 wt % aqueous solution) | 40.0 | 40.0 | 40.0 |
| palm oil fattyacid diethanolamide | 3.0 | 3.0 | 3.0 |
| propyleneglycol | 2.0 | 2.0 | 2.0 |
| methyl paraoxybenzoic acid | 0.2 | 0.2 | 0.2 |
| ehtanol | 2.0 | 2.0 | 2.0 |
| [N-methyl-D-$Nva^3$] cyclosporin A | 1.0 | 3.0 | 10.0 |
| salicylic acid | 0.3 | 0.3 | 0.3 |
| L-menthol | 0.3 | 0.3 | 0.3 |
| flavor | typical | typical | typical |
| colorant | typical | typical | typical |
| water | balance | balance | balance |

3–3: Preparation of Shampoo Containing [D-2-(methylamino)hexa-4-$ynoyl^3$] Cyclosporin A All individual ingredients, except flavor, colorant and water, were mixed and the mixture was completely dissolved by heating, while stirring. After cooling to room temperature, the mixture was mixed with flavor and colorant. Water was finally added to adjust to 100% the total weight, to prepare three shampoos, with compositions as shown in Table 17 below.

TABLE 17

| Formulation of shampoo | | | |
|---|---|---|---|
| | (unit: weight %) | | |
| Ingredients | Comp. 1 | Comp. 2 | Comp. 3 |
| sodium POE laurylsulfuric acid (30 wt % aqueous solution) | 40.0 | 40.0 | 40.0 |
| palm oil fattyacid diethanolamide | 3.0 | 3.0 | 3.0 |
| Propyleneglycol | 2.0 | 2.0 | 2.0 |
| methyl paraoxybenzoic acid | 0.2 | 0.2 | 0.2 |
| Ethanol | 2.0 | 2.0 | 2.0 |
| [D-2-(methylamino)hexa-4-ynoyl$^3$] cyclosporin A | 1.0 | 3.0 | 10.0 |
| salicylic acid | 0.3 | 0.3 | 0.3 |
| L-menthol | 0.3 | 0.3 | 0.3 |
| Flavor | typical | typical | typical |
| Colorant | typical | typical | typical |
| Water | balance | balance | balance |

3–4: Preparation of Shampoo Containing [D-2-(methylamino)pent-4-ynoyl$^3$] Cyclosporin A All individual ingredients, except flavor, colorant and water, were mixed and the mixture was completely dissolved by heating, while stirring. After cooling to room temperature, the mixture was mixed with flavor and colorant. Water was finally added to adjust to 100% the total weight, to prepare three shampoos, with compositions as shown in Table 18 below.

TABLE 18

| Formulation of shampoo | | | |
|---|---|---|---|
| | (unit: weight %) | | |
| Ingredients | Comp. 1 | Comp. 2 | Comp. 3 |
| sodium POE laurylsulfuric acid (30 wt % aqueous solution) | 40.0 | 40.0 | 40.0 |
| palm oil fattyacid diethanolamide | 3.0 | 3.0 | 3.0 |
| propyleneglycol | 2.0 | 2.0 | 2.0 |
| methyl paraoxybenzoic acid | 0.2 | 0.2 | 0.2 |
| ehtanol | 2.0 | 2.0 | 2.0 |
| [D-2-(methylamino)pent-4-ynoyl$^3$] cyclosporin A | 1.0 | 3.0 | 10.0 |
| salicylic acid | 0.3 | 0.3 | 0.3 |
| L-menthol | 0.3 | 0.3 | 0.3 |
| flavor | typical | typical | typical |
| colorant | typical | typical | typical |
| water | balance | balance | balance |

3–5: Preparation of Shampoo Containing [D-2-methylthio-Sar$^3$] Cyclosporin A

All individual ingredients, except flavor, colorant and water, were mixed and the mixture was completely dissolved by heating, while stirring. After cooling to room temperature, the mixture was mixed with flavor and colorant. Water was finally added to adjust to 100% the total weight, to prepare three shampoos, with compositions as shown in Table 19 below.

TABLE 19

| Formulation of shampoo | | | |
|---|---|---|---|
| | (unit: weight %) | | |
| Ingredients | Comp. 1 | Comp. 2 | Comp. 3 |
| sodium POE laurylsulfuric acid (30 wt % aqueous solution) | 40.0 | 40.0 | 40.0 |

TABLE 19-continued

| Formulation of shampoo | | | |
|---|---|---|---|
| | (unit: weight %) | | |
| Ingredients | Comp. 1 | Comp. 2 | Comp. 3 |
| palm oil fattyacid diethanolamide | 3.0 | 3.0 | 3.0 |
| propyleneglycol | 2.0 | 2.0 | 2.0 |
| methyl paraoxybenzoic acid | 0.2 | 0.2 | 0.2 |
| ehtanol | 2.0 | 2.0 | 2.0 |
| [D-2-methylthio-Sar$^3$] cyclosporin A | 1.0 | 3.0 | 10.0 |
| salicylic acid | 0.3 | 0.3 | 0.3 |
| L-menthol | 0.3 | 0.3 | 0.3 |
| flavor | typical | typical | typical |
| colorant | typical | typical | typical |
| water | balance | balance | balance |

3–6: Preparation of Shampoo Containing [N-methyl-O-propenyl-D-Ser$^3$] Cyclosporin A All individual ingredients, except flavor, colorant and water, were mixed and the mixture was completely dissolved by heating, while stirring. After cooling to room temperature, the mixture was mixed with flavor and colorant. Water was finally added to adjust to 100% the total weight, to prepare three shampoos, with compositions as shown in Table 20 below.

TABLE 20

| Formulation of shampoo | | | |
|---|---|---|---|
| | (unit: weight %) | | |
| Ingredients | Comp. 1 | Comp. 2 | Comp. 3 |
| sodium POE laurylsulfuric acid (30 wt % aqueous solution) | 40.0 | 40.0 | 40.0 |
| palm oil fattyacid diethanolamide | 3.0 | 3.0 | 3.0 |
| propyleneglycol | 2.0 | 2.0 | 2.0 |
| methyl paraoxybenzoic acid | 0.2 | 0.2 | 0.2 |
| ehtanol | 2.0 | 2.0 | 2.0 |
| [N-methyl-O-propenyl-D-Ser$^3$] cyclosporin A | 1.0 | 3.0 | 10.0 |
| salicylic acid | 0.3 | 0.3 | 0.3 |
| L-menthol | 0.3 | 0.3 | 0.3 |
| flavor | typical | typical | typical |
| colorant | typical | typical | typical |
| water | balance | balance | balance |

3–7: Preparation of Shampoo Containing [N-methyl-D-Ser$^3$] Cyclosporin A

All individual ingredients, except flavor, colorant and water, were mixed and the mixture was completely dissolved by heating, while stirring. After cooling to room temperature, the mixture was mixed with flavor and colorant. Water was finally added to adjust to 100% the total weight, to prepare three shampoos, with compositions as shown in Table 21 below.

TABLE 21

| Formulation of shampoo | | | |
|---|---|---|---|
| | (unit: weight %) | | |
| Ingredients | Comp. 1 | Comp. 2 | Comp. 3 |
| sodium POE laurylsulfuric acid (30 wt % aqueous solution) | 40.0 | 40.0 | 40.0 |
| palm oil fattyacid diethanolamide | 3.0 | 3.0 | 3.0 |
| propyleneglycol | 2.0 | 2.0 | 2.0 |
| methyl paraoxybenzoic acid | 0.2 | 0.2 | 0.2 |

TABLE 21-continued

Formulation of shampoo

| Ingredients | Comp. 1 | Comp. 2 | Comp. 3 |
|---|---|---|---|
| | (unit: weight %) | | |
| ehtanol | 2.0 | 2.0 | 2.0 |
| [N-methyl-D-Ser$^3$] cyclosporin A | 1.0 | 3.0 | 10.0 |
| salicylic acid | 0.3 | 0.3 | 0.3 |
| L-menthol | 0.3 | 0.3 | 0.3 |
| flavor | typical | typical | typical |
| colorant | typical | typical | typical |
| water | balance | balance | balance |

PREPARATIVE EXAMPLE 4

Hair Conditioner 4-1: Preparation of Hair Conditioner Containing [N-methyl-D-Abu 3] Cyclosporin A Individual oil-phase and water-phase ingredients were mixed in a separate container, and each mixture was completely dissolved by heating to 80° C. Two phases of the ingredients were mixed, emulsified, and cooled to room temperature. Additives such as flavor and colorant were admixed to prepare three hair conditioners, with compositions as shown in Table 22 below. Water was added to adjust to 100% the total weight including the oil-phase and water-phase ingredients.

TABLE 22

Formulation of hair conditioner

| Ingredients | Comp. 1 | Comp. 2 | Comp. 3 |
|---|---|---|---|
| | (unit: weight %) | | |
| Cetanol | 3.0 | 3.0 | 3.0 |
| self-emulsifiable glycerol-monostearate | 2.0 | 2.0 | 3.0 |
| Squalene | 10.0 | 10.0 | 10.0 |
| [N-methyl-D-Abu$^3$] cyclosporin A | 1.0 | 5.0 | 10.0 |
| Propyleneglycol | 2.0 | 2.0 | 2.0 |
| stearyldimethyl benzylammonium chloride (25 wt % aqueous solution) | 8.0 | 8.0 | 8.0 |
| methyl paraoxybenzoic acid | 0.2 | 0.2 | 0.2 |
| salicylic acid | 0.3 | 0.3 | 0.3 |
| L-menthol | 0.3 | 0.3 | 0.3 |
| Water | balance | balance | balance |
| Flavor | typical | typical | typical |
| Colorant | typical | typical | typical |

4-2: Preparation of Hair Conditioner Containing [N-methyl-D-Nva$^3$] Cyclosporin A Individual oil-phase and water-phase ingredients were mixed in a separate container, and each mixture was completely dissolved by heating to 80° C. Two phases of the ingredients were mixed, emulsified, and cooled to room temperature. Additives such as flavor and colorant were admixed to prepare three hair conditioners, with compositions as shown in Table 23 below. Water was added to adjust to 100% the total weight including the oil-phase and water-phase ingredients.

TABLE 23

Formulation of hair conditioner

| Ingredients | Comp. 1 | Comp. 2 | Comp. 3 |
|---|---|---|---|
| | (unit: weight %) | | |
| Cetanol | 3.0 | 3.0 | 3.0 |
| self-emulsifiable glycerol-monostearate | 2.0 | 2.0 | 3.0 |
| Squalene | 10.0 | 10.0 | 10.0 |
| [N-methyl-D-Nva$^3$] cyclosporin A | 1.0 | 5.0 | 10.0 |
| Propyleneglycol | 2.0 | 2.0 | 2.0 |
| stearyldimethyl benzylammonium chloride (25 wt % aqueous solution) | 8.0 | 8.0 | 8.0 |
| methyl paraoxybenzoic acid | 0.2 | 0.2 | 0.2 |
| salicylic acid | 0.3 | 0.3 | 0.3 |
| L-menthol | 0.3 | 0.3 | 0.3 |
| Water | balance | balance | balance |
| Flavor | typical | typical | typical |
| Colorant | typical | typical | typical |

4-3: Preparation of Hair Conditioner Containing [D-2-(methylamino)hexa-4-ynoyl$^3$] Cyclosporin A Individual oil-phase and water-phase ingredients were mixed in a separate container, and each mixture was completely dissolved by heating to 80° C. Two phases of the ingredients were mixed, emulsified, and cooled to room temperature. Additives such as flavor and colorant were admixed to prepare three hair conditioners, with compositions as shown in Table 24 below. Water was added to adjust to 100% the total weight including the oil-phase and water-phase ingredients.

TABLE 24

Formulation of hair conditioner

| Ingredients | Comp. 1 | Comp. 2 | Comp. 3 |
|---|---|---|---|
| | (unit: weight %) | | |
| Cetanol | 3.0 | 3.0 | 3.0 |
| self-emulsifiable glycerol-monostearate | 2.0 | 2.0 | 3.0 |
| Squalene | 10.0 | 10.0 | 10.0 |
| [D-2-(methylamino)hexa-4-ynoyl$^3$] cyclosporin A | 1.0 | 5.0 | 10.0 |
| Propyleneglycol | 2.0 | 2.0 | 2.0 |
| stearyldimethyl benzylammonium chloride (25 wt % aqueous solution) | 8.0 | 8.0 | 8.0 |
| methyl paraoxybenzoic acid | 0.2 | 0.2 | 0.2 |
| salicylic acid | 0.3 | 0.3 | 0.3 |
| L-menthol | 0.3 | 0.3 | 0.3 |
| Water | balance | balance | balance |
| Flavor | typical | typical | typical |
| Colorant | typical | typical | typical |

4-4: Preparation of Hair Conditioner Containing [D-2-(methylamino)pent-4-ynoyl$^3$] Cyclosporin Individual oil-phase and water-phase ingredients were mixed in a separate container, and each mixture was completely dissolved by heating to 80° C. Two phases of the ingredients were mixed, emulsified, and cooled to room temperature. Additives such as flavor and colorant were admixed to prepare three hair conditioners, with compositions as shown in Table 25 below. Water was added to adjust to 100% the total weight including the oil-phase and water-phase ingredients.

TABLE 25

Formulation of hair conditioner

| Ingredients | Comp. 1 (unit: weight %) | Comp. 2 | Comp. 3 |
|---|---|---|---|
| Cetanol | 3.0 | 3.0 | 3.0 |
| self-emulsifiable glycerol-monostearate | 2.0 | 2.0 | 3.0 |
| Squalene | 10.0 | 10.0 | 10.0 |
| [D-2-(methylamino)pent-4-ynoyl$^3$] cyclosporin A | 1.0 | 5.0 | 10.0 |
| Propyleneglycol | 2.0 | 2.0 | 2.0 |
| stearyldimethyl benzylammonium chloride (25 wt % aqueous solution) | 8.0 | 8.0 | 8.0 |
| methyl paraoxybenzoic acid | 0.2 | 0.2 | 0.2 |
| salicylic acid | 0.3 | 0.3 | 0.3 |
| L-menthol | 0.3 | 0.3 | 0.3 |
| Water | balance | balance | balance |
| Flavor | typical | typical | typical |
| Colorant | typical | typical | typical |

4–5: Preparation of Hair Conditioner Containing [D-2-methylthio-Sar$^3$] Cyclosporin A Individual oil-phase and water-phase ingredients were mixed in a separate container, and each mixture was completely dissolved by heating to 80° C. Two phases of the ingredients were mixed, emulsified, and cooled to room temperature. Additives such as flavor and colorant were admixed to prepare three hair conditioners, with compositions as shown in Table 26 below. Water was added to adjust to 100% the total weight including the oil-phase and water-phase ingredients.

TABLE 26

Formulation of hair conditioner

| Ingredients | Comp. 1 (unit: weight %) | Comp. 2 | Comp. 3 |
|---|---|---|---|
| Cetanol | 3.0 | 3.0 | 3.0 |
| self-emulsifiable glycerol-monostearate | 2.0 | 2.0 | 3.0 |
| Squalene | 10.0 | 10.0 | 10.0 |
| [D-2-methylthio-Sar$^3$] cyclosporin A | 1.0 | 5.0 | 10.0 |
| Propyleneglycol | 2.0 | 2.0 | 2.0 |
| stearyldimethyl benzylammonium chloride (25 wt % aqueous solution) | 8.0 | 8.0 | 8.0 |
| methyl paraoxybenzoic acid | 0.2 | 0.2 | 0.2 |
| salicylic acid | 0.3 | 0.3 | 0.3 |
| L-menthol | 0.3 | 0.3 | 0.3 |
| Water | balance | balance | balance |
| Flavor | typical | typical | typical |
| Colorant | typical | typical | typical |

4–6: Preparation of Hair Conditioner Containing [N-methyl-O-propenyl-D-Ser$^3$] Cyclosporin A Individual oil-phase and water-phase ingredients were mixed in a separate container, and each mixture was completely dissolved by heating to 80° C. Two phases of the ingredients were mixed, emulsified, and cooled to room temperature. Additives such as flavor and colorant were admixed to prepare three hair conditioners, with compositions as shown in Table 27 below. Water was added to adjust to 100% the total weight including the oil-phase and water-phase ingredients.

TABLE 27

Formulation of hair conditioner

| Ingredients | Comp. 1 (unit: weight %) | Comp. 2 | Comp. 3 |
|---|---|---|---|
| Cetanol | 3.0 | 3.0 | 3.0 |
| self-emulsifiable glycerol-monostearate | 2.0 | 2.0 | 3.0 |
| Squalene | 10.0 | 10.0 | 10.0 |
| [N-methyl-O-propenyl-D-Ser$^3$] cyclosporin A | 1.0 | 5.0 | 10.0 |
| Propyleneglycol | 2.0 | 2.0 | 2.0 |
| stearyldimethyl benzylammonium chloride (25 wt % aqueous solution) | 8.0 | 8.0 | 8.0 |
| methyl paraoxybenzoic acid | 0.2 | 0.2 | 0.2 |
| salicylic acid | 0.3 | 0.3 | 0.3 |
| L-menthol | 0.3 | 0.3 | 0.3 |
| Water | balance | balance | balance |
| Flavor | typical | typical | typical |
| Colorant | typical | typical | typical |

4–7: Preparation of Hair Conditioner Containing [N-methyl-D-Ser$^3$] Cyclosporin A Individual oil-phase and water-phase ingredients were mixed in a separate container, and each mixture was completely dissolved by heating to 80° C. Two phases of the ingredients were mixed, emulsified, and cooled to room temperature. Additives such as flavor and colorant were admixed to prepare three hair conditioners, with compositions as shown in Table 28 below. Water was added to adjust to 100% the total weight including the oil-phase and water-phase ingredients.

TABLE 28

Formulation of hair conditioner

| Ingredients | Comp. 1 (unit: weight %) | Comp. 2 | Comp. 3 |
|---|---|---|---|
| Cetanol | 3.0 | 3.0 | 3.0 |
| self-emulsifiable glycerol-monostearate | 2.0 | 2.0 | 3.0 |
| Squalane | 10.0 | 10.0 | 10.0 |
| [N-methyl-D-Ser$^3$] cyclosporin A | 1.0 | 5.0 | 10.0 |
| Propyleneglycol | 2.0 | 2.0 | 2.0 |
| stearyldimethyl benzylammonium chloride (25 wt % aqueous solution) | 8.0 | 8.0 | 8.0 |
| methyl paraoxybenzoic acid | 0.2 | 0.2 | 0.2 |
| salicylic acid | 0.3 | 0.3 | 0.3 |
| L-menthol | 0.3 | 0.3 | 0.3 |
| Water | balance | balance | balance |
| Flavor | typical | typical | typical |
| Colorant | typical | typical | typical |

TEST EXAMPLE

Test for Hair Growth Promoting Effect of Cyclosporin Derivatives of the Invention Female C57BL/6 mice of ages 6 to 7 weeks were utilized. After removing hairs on the middle of the back with an electric shaver, the mice were weighed and randomly assigned to the test groups with an even distribution of weights. The mice were given one day for adaptation. From the next day, mice were applied once a day on their backs with cyclosporin A and the cyclosporin A derivatives (Compounds 1 to 7) prepared by HPLC in Example 1 in amounts of 100 $\mu$l (conc. 0.1% w/v) for 30 days. The results were determined by visual approach, in terms of degrees of hair regrowth. With respect to respective hair-removed areas, rates of new hair growth were examined and compared.

As can be seen in Table 29, cyclosporin derivatives of the invention have a significant hair growth promoting effect, compared to the control in which mice were applied with a vehicle only. Further, the derivatives show a similar level of hair growth promoting effect, with respect to cyclosporin A. Meanwhile, over a course of 30 days, as comparing the appearance of the backs, the mice of the control and all test groups showed no specific skin irritation.

TABLE 29

Evaluation of cyclosporin derivatives based on hair regrowth in mice

| Compound applied | Vehicle | cyclosporin A | 1 | 2 | 3 | 4 | 5 | 6 | 7 |
|---|---|---|---|---|---|---|---|---|---|
| Area rate of hair regrowth (%) | 35 | 91 | 95 | 91 | 95 | 96 | 93 | 94 | 90 |

On the basis of the foregoing results, the cyclosporin derivatives of the invention may be formulated in any form including liquid formulations, sprays, gels, pastes, emulsions, creams, conditioners, shampoos, and the like. A variety of forms are available though, considering their high commercial demand, hair tonics, creams, conditioners, and shampoos are provided herein. As revealed in the above the Test Example, the cyclosporin derivatives exhibit an excellent hair growth promoting effect, compared to the control.

INDUSTRIAL APPLICABILITY

As apparent from the above description, the present invention provides a hair growth promoting agent comprising a cyclosporin A derivative substituted in the 3-position of cyclosporin A as an active ingredient, which exhibits an excellent hair growth promoting effect.

What is claimed is:

1. A method for treating alopecia and promoting hair growth comprising treating a patient in need thereof with a pharmaceutical composition containing a 3-position analog of cyclosporin represented by Formula 3, as an active ingredient:

[Formula 3]

MeBmt—A″—B″—MeLeu-Val-MeLeu-Ala-DAla-MeLeu-MeLeu-MeVal in which

MeBmt represents N-methyl-(4R)-4-[(E)-2-butenyl]-4-methyl-L-threonine;

A″ represents L-aminobutyric acid (Abu);

B″ represents a D-amino acid represented by the general formula 1, $$CH_3NH-CH(R)-COOH \qquad \text{[General Formula 1]}$$

in which,

R represents X-R′ of the general formula 2 below, $$-X-R' \qquad \text{[General Formula 2]}$$

in which,

X is oxygen or sulfur, and

R is selected from the group consisting of hydrogen, and $C_1$–$C_6$ straight or branched alkyl, alkenyl or alkynyl moieties, substituted or unsubstituted with one or more selected from the group consisting of amino, hydroxy, halo, haloalkyl, ester, alkoxy, cyano, nitro, alkylamino, and dialkylamino, with the proviso that when X is sulfur, R′ is methyl, substituted or unsubstituted with one or more selected from the group consisting of amino, hydroxy, halo, haloalyl, ester, alkoxy, cyano, nitro, alklamino, and dialkylamino;

MeLeu represents N-methyl-L-leucine

Val represents L-valine;

Ala represents L-alanine;

DAla represents D-alanine; and

MeVal represents N-methyl-L-valine.

2. The method of claim 1 wherein said composition contains [D-2-methylthio-sarcosine³] cyclosporin A as an active ingredient.

3. The method of claim 1 wherein said composition is formulated in a form selected from the group consisting of liquid formulation, spray, gel, paste, emulsion, cream, conditioner and shampoo.

4. The method of claim 2 wherein said composition is formulated in a form selected from the group consisting of liquid formulation, spray, gel, paste, emulsion, cream, conditioner and shampoo.

* * * * *

UNITED STATES PATENT AND TRADEMARK OFFICE
CERTIFICATE OF CORRECTION

PATENT NO. : 6,762,164 B2
DATED : July 13, 2004
INVENTOR(S) : Kim et al.

It is certified that error appears in the above-identified patent and that said Letters Patent is hereby corrected as shown below:

Column 24,
Line 19, "R is selected" should read -- R' is selected --

Signed and Sealed this

Twenty-first Day of December, 2004

JON W. DUDAS
*Director of the United States Patent and Trademark Office*